US 7,766,630 B2

(12) United States Patent
Fathallah et al.

(10) Patent No.: US 7,766,630 B2
(45) Date of Patent: Aug. 3, 2010

(54) FLUID DELIVERY DEVICE IDENTIFICATION AND LOADING SYSTEM

(75) Inventors: Marwan A. Fathallah, Mundelein, IL (US); John Stephen Ziegler, Arlington Heights, IL (US); David C. Franchino, Madison, WI (US); Todd J. Bakken, Madison, WI (US); Kent B. Chase, Madison, WI (US); Daniel J. Lee, Madison, WI (US)

(73) Assignee: Hospira, Inc., Lake Forest, IL (US)

( * ) Notice: Subject to any disclaimer, the term of this patent is extended or adjusted under 35 U.S.C. 154(b) by 216 days.

(21) Appl. No.: 11/835,798

(22) Filed: Aug. 8, 2007

(65) Prior Publication Data
US 2008/0038130 A1 Feb. 14, 2008

Related U.S. Application Data

(62) Division of application No. 10/667,611, filed on Sep. 22, 2003, now Pat. No. 7,258,534.

(51) Int. Cl.
*F04B 43/12* (2006.01)

(52) U.S. Cl. ............... 417/477.2; 417/474; 417/477.1; 604/153

(58) Field of Classification Search ............... 417/63, 417/395, 413.1, 477.2, 474, 477.1; 604/141, 604/151, 153
See application file for complete search history.

(56) References Cited

U.S. PATENT DOCUMENTS

| 4,187,057 A | 2/1980 | Xanthopoulos |
| 4,236,880 A * | 12/1980 | Archibald .................. 417/478 |
| 4,303,376 A * | 12/1981 | Siekmann .................. 417/360 |
| 5,282,787 A | 2/1994 | Wortrich |
| 5,462,256 A | 10/1995 | Minick et al. |
| 5,586,868 A | 12/1996 | Lawless et al. |
| 5,647,852 A | 7/1997 | Atkinson |
| 5,673,588 A | 10/1997 | Raymond |
| 5,816,779 A | 10/1998 | Lawless et al. |
| 5,954,485 A * | 9/1999 | Johnson et al. ............. 417/474 |
| 5,989,222 A * | 11/1999 | Cole et al. .................. 604/151 |
| 6,056,522 A * | 5/2000 | Johnson ..................... 417/474 |
| 6,231,320 B1 | 5/2001 | Lawless et al. |
| 6,595,943 B1 | 7/2003 | Burbank |
| 6,942,473 B2 * | 9/2005 | Abrahamson et al. ....... 417/474 |

(Continued)

FOREIGN PATENT DOCUMENTS

WO 93/12828 8/1993

*Primary Examiner*—Devon C Kramer
*Assistant Examiner*—Leonard J Weinstein
(74) *Attorney, Agent, or Firm*—Michael R. Crabb

(57) ABSTRACT

A medical pump includes a chassis having a fixed seat, and a main carriage having a carriage footing for receiving a fluid delivery device and restricting its movement. An actuator automatically moves the main carriage between open and closed positions to engage the fluid delivery device to the seat. The seat establishes the position of both the main carriage and fluid delivery device in the closed position. The actuator is connected to the main carriage by a rear carriage assembly having a manual release element for disengaging the actuator from rear carriage assembly and thereby from the main carriage. A processing unit detects jam conditions by processing carriage position data and electrical load data from the actuator.

7 Claims, 19 Drawing Sheets

U.S. PATENT DOCUMENTS

| | | | |
|---|---|---|---|
| 7,041,076 B1 * | 5/2006 | Westberg et al. | 604/6.01 |
| 2003/0138349 A1 | 7/2003 | Robinson et al. | |
| 2003/0175820 A1 * | 9/2003 | Smith et al. | 435/7.2 |
| 2003/0202894 A1 * | 10/2003 | Leukanech et al. | 417/477.2 |

* cited by examiner

FLUID DELIVERY DEVICE IDENTIFICATION AND LOADING SYSTEM

CROSS REFERENCE TO RELATED APPLICATION

This application is a divisional of U.S. Ser. No. 10/667,611 filed on Sep. 22, 2003.

BACKGROUND OF THE INVENTION

The present invention relates to a means of automatically loading and unloading a pump cassette or other fluid delivery device into a medical pump.

Modern medical care often involves the use of medical pump devices to deliver fluids and/or fluid medicine to patients. Medical pumps permit the controlled delivery of fluids to a patient, and such pumps have largely replaced gravity flow systems, primarily due to the pump's much greater accuracy in delivery rates and dosages, and due to the possibility for flexible yet controlled delivery schedules. Of the modern medical pumps, those incorporating a diaphragm cassette are often preferred because they provide more accurately controlled rate and volume than do other types of pumps.

A typical positive displacement pump system includes a pump device driver and a fluid delivery device, including but not limited to a syringe, tubing, section of tubing, or a disposable cassette. The disposable cassette, which is adapted to be used only for a single patient and for one fluid delivery cycle, is typically a small plastic unit having an inlet and an outlet respectively connected through flexible tubing to a fluid supply container and to the patient receiving the fluid. The cassette includes a pumping chamber, with the flow of fluid through the chamber being controlled by a plunger or plunger activated in a controlled manner by the device driver.

One of the requirements for many pumps, including cassette pumps, is that they are able to dictate the proper positioning of the fluid delivery device or cassette when loaded. The proper positioning of the cassette is critical to ensure that any pump elements (including the plunger and/or sensors) that interact with the cassette are precisely aligned and positioned to accurately produce the desired output of the cassette or sense conditions related to the pump.

Previous pumps attempted to accomplish the proper positioning of the cassette by providing a molded seat that a user would manually push the cassette into. Once the cassette is forced into the molded seat, retentive snap elements engage the outer surface of the cassette to hold the cassette within the molded seat.

These previous pumps often have few if any physical elements to ensure proper cassette orientation to the pump. They also do not ensure proper and complete seating of the cassette to the pump. Additionally, they have insufficient means for monitoring if the cassette was indeed oriented correctly and/or fully seated to the pump.

Therefore, a principal object of this invention is to provide a medical pump having an automated loading system with improved positioning of the fluid delivery device.

A further object of the invention is to provide a medical pump that monitors proper fluid delivery device loading.

Another object of the invention is to provide a medical pump having an indicator window for indicating channel conditions.

A still further object of the invention is to provide a medical pump having an illumination element for illuminating a main carriage area where the fluid delivery device is loaded.

Another object of the invention is to provide a medical pump having a manual release element for manually ejecting a fluid delivery device from the pump.

These and other objects will be apparent to those skilled in the art.

SUMMARY OF THE INVENTION

A medical pump includes a chassis having a fixed seat, and a main carriage having a carriage footing for receiving a fluid delivery device, including but not limited to a cassette, syringe and/or tubing, and restricting its movement. An orientation sensor determines the correct insertion of the fluid delivery device in the carriage. An indicator window includes an illumination element for illuminating a main carriage area and a multicolor indicator element for illuminating the indicator window. An actuator automatically moves the main carriage between open and closed positions to engage the cassette to the fluid delivery device seat. The seat establishes the position of both the main carriage and fluid delivery device in the closed position. The actuator is connected to the main carriage by a rear carriage assembly having a manual release element for disengaging the actuator from rear carriage assembly and thereby from the main carriage. A processing unit detects jam conditions by processing carriage position data and electrical load data from the actuator.

DETAILED DESCRIPTION OF THE PREFERRED EMBODIMENT

Figure 1:
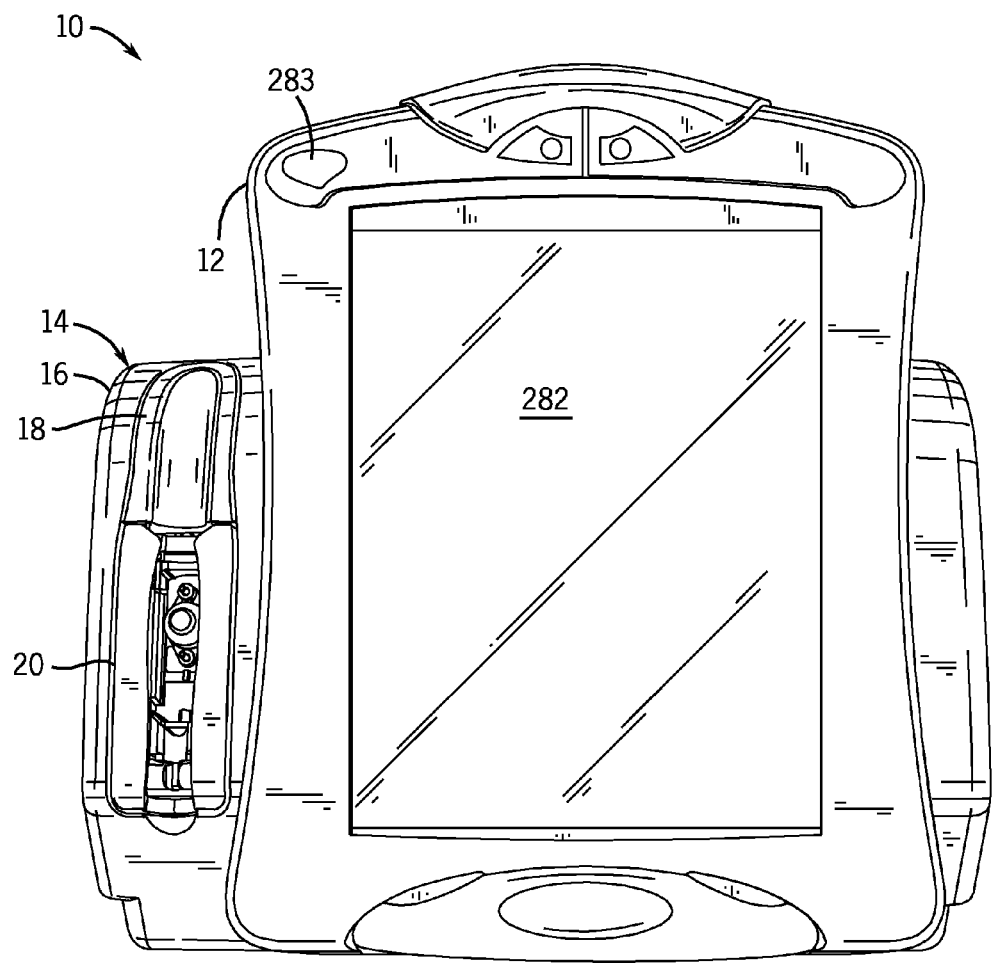
FIG. 1 is a front view of the medical pump of the present invention.

With reference to FIG. 1, a medical pump 10 is shown having a housing 12 and an infuser mechanism 14 attached to the housing 12. The infuser mechanism 14 includes an infuser cover 16, an indicator window 18 attached to the infuser cover 16, and a loader 20 for a fluid delivery device, including but not limited to a cassette, syringe, and/or tubing. The loader 20 is attached to the infuser cover 16 immediately below the indicator window 18.

Figure 2:
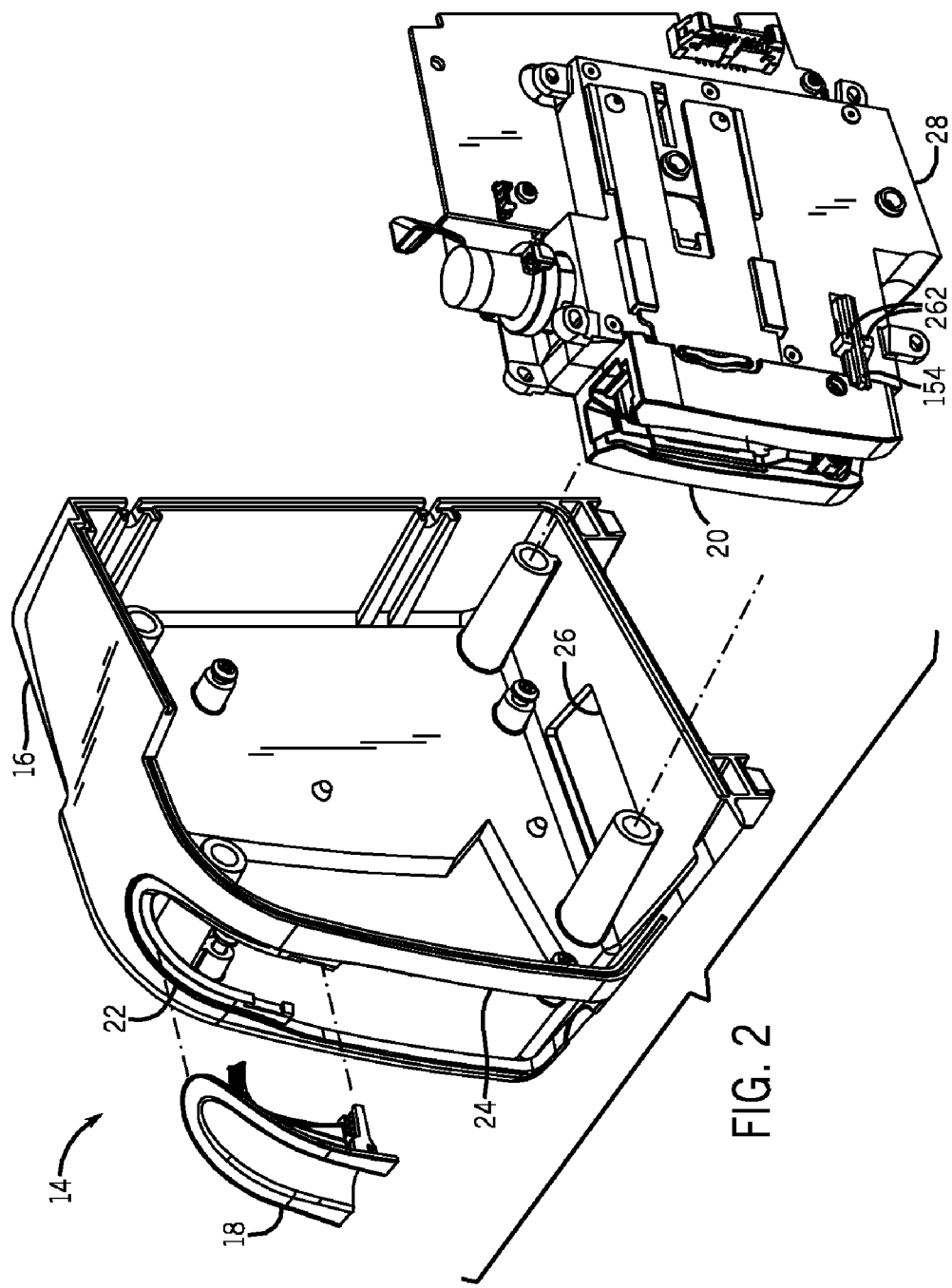
FIG. 2 is an exploded perspective view of an infuser mechanism of the present invention.

With reference to FIG. 2, indicator opening 22, loader opening 24, and manual release opening 26 are all formed in the infuser cover 16. The indicator opening 22 permits insertion and attachment of the indicator window 18 to the infuser cover 16. Likewise, the loader opening 24 permits insertion and attachment of the loader 20 to the infuser cover 16. The manual release opening 26 permits insertion and attachment of a manual release portion 28 of the loader 20 to the infuser cover 16.

Figure 3:
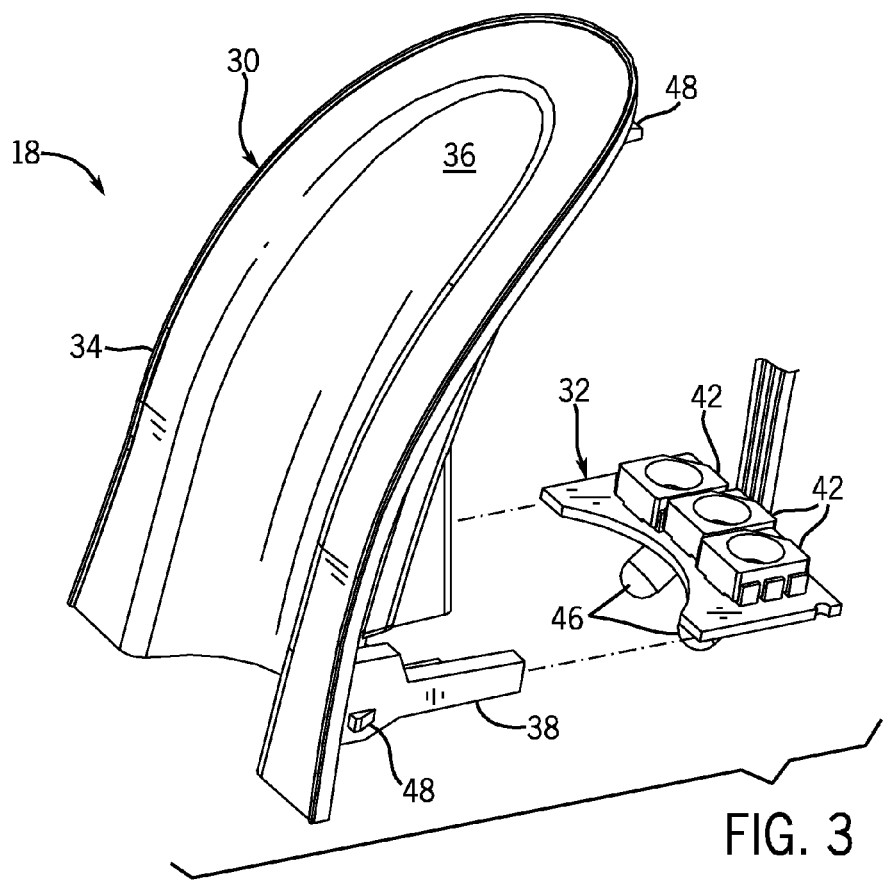
FIG. 3 is an exploded perspective view of an indicator window of the present invention.
Figure 4:
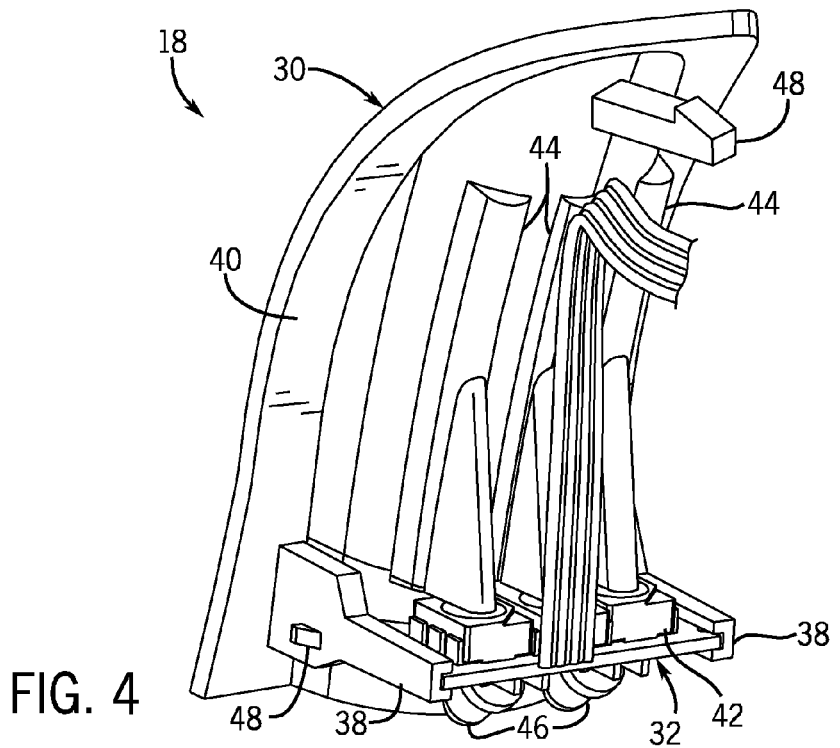
FIG. 4 is a rear perspective view of an indicator window of the present invention.

With reference to FIGS. 3 and 4, a window body 30 and light assembly 32 form the indicator window 18. The window body 30 is formed of a transparent or translucent material which facilitates the diffusion and transmission of light therethrough. The window body 30 has an outer surface 34 that includes a groove shaped portion 36. The groove shaped portion 36 is shown as being concave, but may be formed in any suitable shape. The groove shaped portion 36 provides clearance for a user to smoothly route an inlet tube (not shown) to the loader 20.

A pair of rails 38 extends horizontally from an inner surface of the window body 30. The rails 38 secure the light assembly 32 to the window body 30. Several multi-color indicator elements 42 are located on the upper surface of the light assembly 32. These indicator elements 42 are shown as three individual light-emitting diode (LED) lights. The indicator elements 42 are each associated with corresponding light pipes 44.

The light pipes 44 are formed as an integral portion of the inner surface 40 of the window body 30. The light pipes 44 facilitate the even distribution of light from the indicator elements 42 to the outer surface 34 of the window body 30. Due to the multi-color attributes of the indicator elements 42, the outer surface 34 of the window body 30 can be lit up with various colors, and can continuously or intermittently be lit. The coloring and/or flashing is used to provide an indication of the operation conditions of the pump 10.

One or more illumination elements 46 are located on the lower surface of the light assembly 32. These illumination elements 46 are shown as two individual white light LEDs. When the loader 20 is opened for insertion of a cassette, the illumination elements 46 are activated to illuminate the area where the cassette is inserted into the pump 10. The illumination elements 46 may immediately light up or may be designed to gradually illuminate upon opening of the loader 20. The determination of when the loader 20 has been opened will be discussed in greater detail below.

Several snap fasteners 48 extend from the inner surface 40 of the window body 30. These snap fasteners 48 secure the indicator window 18 to the infuser cover 16 in covering relation to the indicator opening 22.

Figure 5:
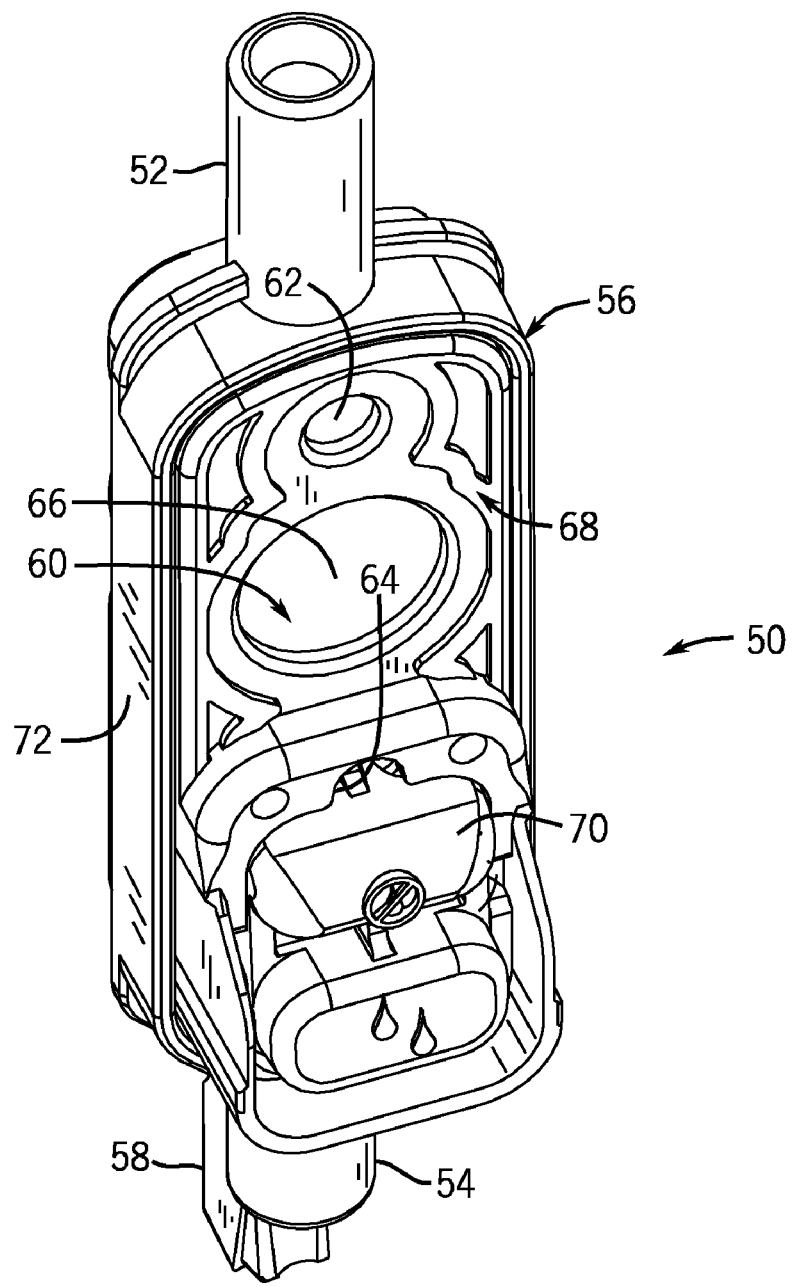
FIG. 5 is a perspective view of a cassette for use with the present invention.

With reference to FIG. 5, one fluid delivery device, such as a cassette 50, suitable for use with the present invention is shown. The cassette 50 includes an inlet 52 and an outlet 54 formed in main body 56. Attached to the outlet 54 is a tube support element 58 for ensuring that tubing (not shown) connected to the outlet 54 is maintained in a proper position with respect to external sensors (not shown).

An elastomeric membrane 60 forms an inlet diaphragm 62, an outlet diaphragm (generally indicated at 64, but only shown in FIG. 21), and a pumping chamber 66 located between the inlet and outlet diaphragms 62 and 64 on an inner face 68 of the main body 56.

In operation, fluid enters through the inlet 52 and is forced through outlet 54 under pressure. The fluid is delivered to the outlet 54 when the pump 10 displaces the pumping chamber 66 to expel the fluid. During the intake stroke the pump 10 releases the pumping chamber 66, and the fluid is then drawn through the inlet 52 and into the pumping chamber 66. In a pumping stroke, the pump 10 displaces the pumping chamber 66 to force the fluid contained therein through the outlet 54. Thus, the fluid flows from the cassette 50 in a series of spaced-apart pulses rather than in a continuous flow. The fluid is delivered to the patient at a pre-set rate, in a pre-determined manner, and only for a particular pre-selected time or total dosage.

A flow stop 70 is formed as a switch in the main body 56 and protrudes from the inner surface 68. This protrusion forms an irregular portion of the inner surface 68 which can be used to align the cassette 50 as well as monitor the orientation of the cassette 50, as will be discussed further below. The flow stop 70 provides a manual switch for closing and opening the cassette 50 to fluid flow.

A rim 72 is located around the outer surface of the main body 56 and adjacent the inner surface 68. The rim 72 is used to secure the cassette in a fixed position relative to the pump 10.

Figure 6:
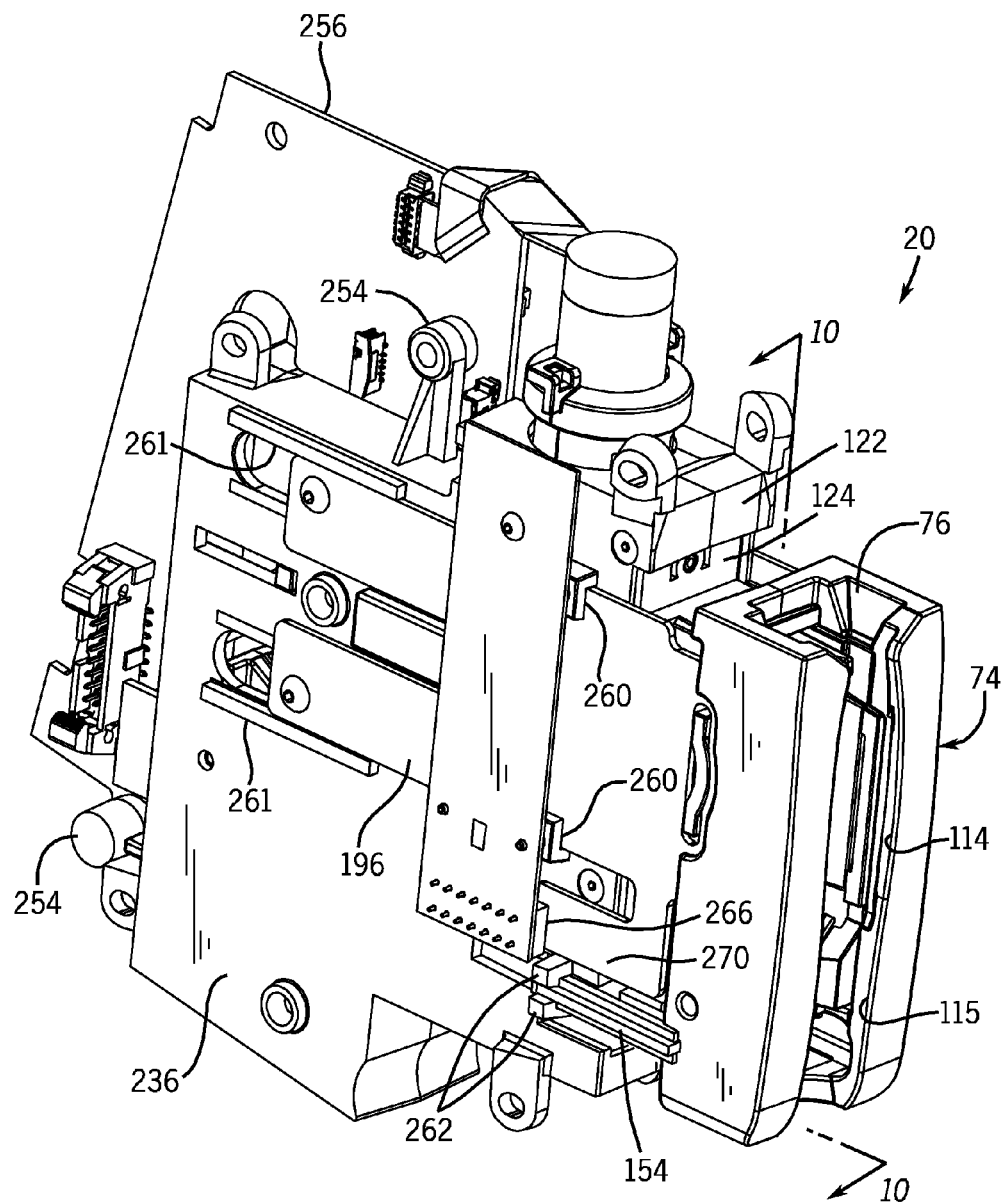
FIG. 6 is a left side perspective view of an open loader with no cassette.

With reference to FIGS. 5 and 6, a front carriage assembly 74 is shown extending from the loader 20. In this extended position, a cassette 50 (not shown) is inserted into a top opening 76 of the front carriage assembly 74.

Figure 7:
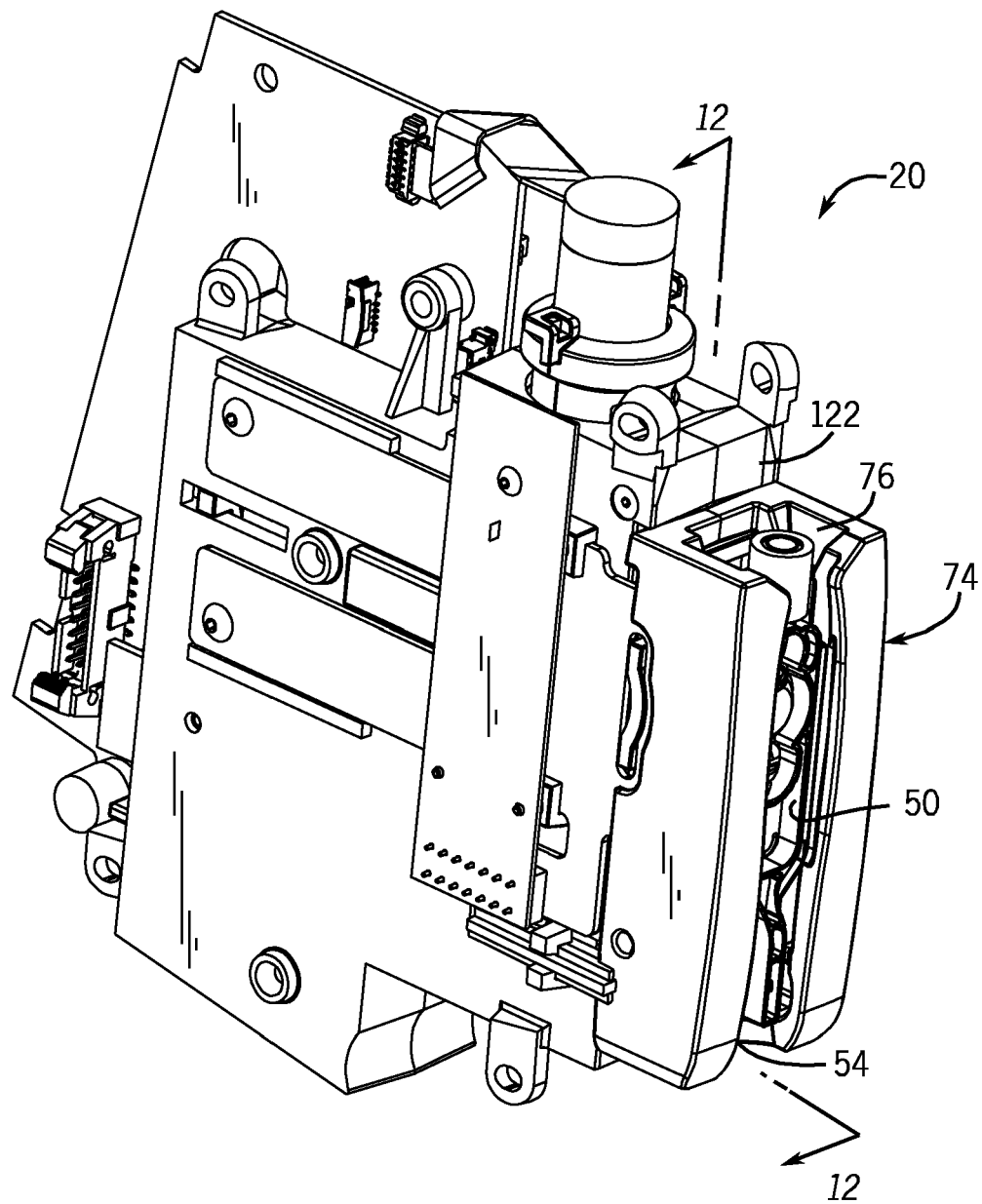
FIG. 7 is a left side perspective view of a closed loader with a cassette.

With reference to FIGS. 5, 6 and 7, the cassette 50 is illustrated in FIG. 5 and the front carriage assembly 74 is shown in an open or extended position (FIG. 6) and then a closed position (FIG. 7). In proper use, top opening 76 first receives the outlet 54 of the cassette 50 with the inner surface 68 facing towards the loader 20.

This proper orientation of the cassette 50 to the loader 20 is essential for proper operation of the pump 10. As will be described in more detail below, the loader 20 of the present invention has been designed to include several mechanical and electronic features to ensure the proper alignment of the cassette 50.

Figure 8:
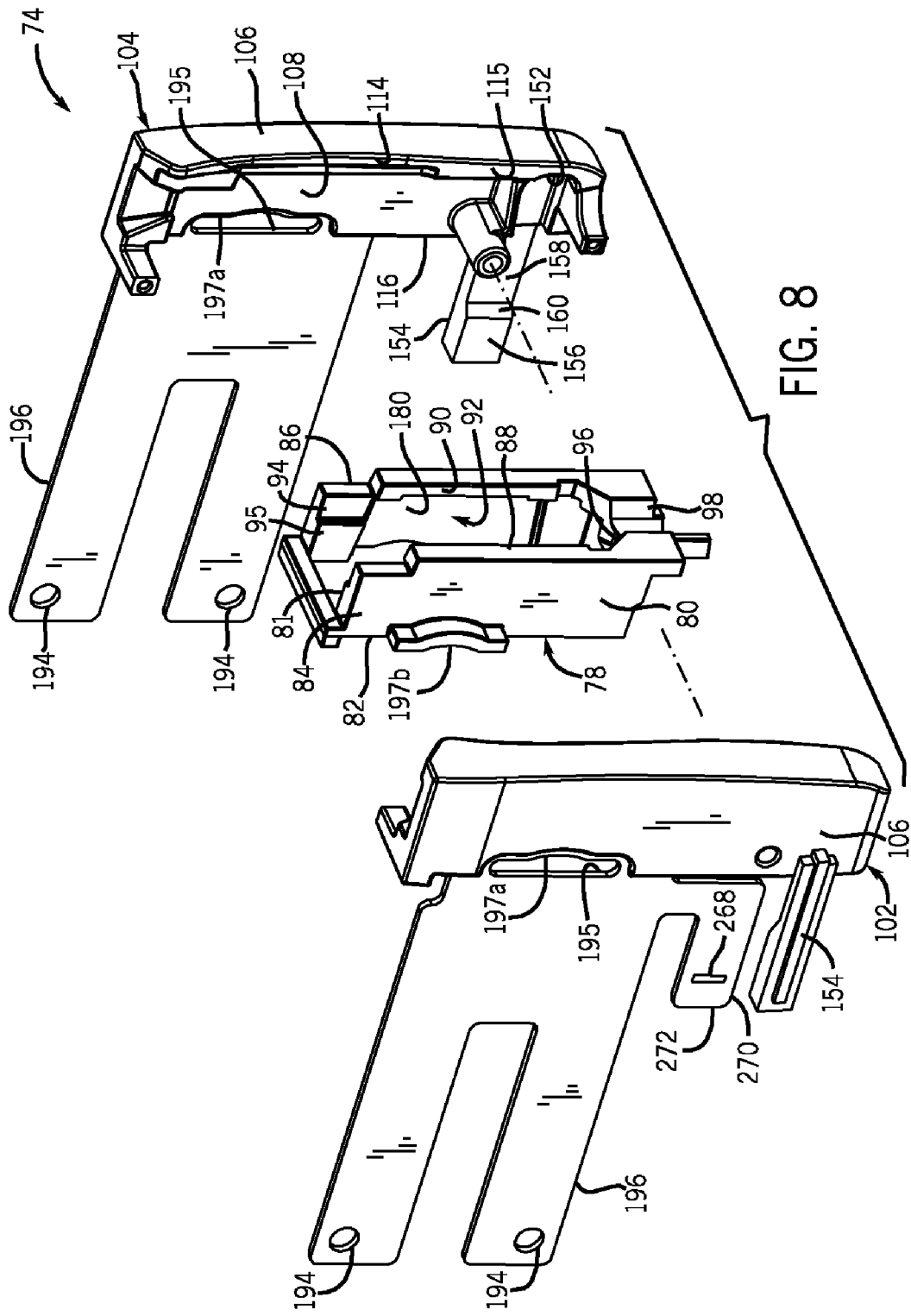
FIG. 8 is a perspective exploded left side view of a front carriage assembly of the present invention.

With reference to FIGS. 5 and 8, a main carriage 78 having a main body 80 with a top opening 81 therein for receiving a cassette 50 as well as an open base surface 82 which permits access to the inner surface 68 of the cassette 50. Left and right vertical side walls 84 and 86 extend horizontally from the base surface 82. Outer lips 88 are positioned opposite the base surface 82 on the end of each side wall 84 and 86. The outer lips 88 define an outer opening 90 in the main body 80. The outer lips 88 abut the rim 72 of an inserted cassette 50 to prevent the cassette 50 from falling out of the outer opening 90, and also enable the main carriage 78 to press the cassette 50 towards the loader 20 by engaging the rim 72.

A cassette footing 92 is formed from portions of the side walls 84 and 86 and the outer lips 88. The cassette footing 92 restricts movement of the cassette 50 within the main carriage 78 to hold the cassette 50 in a desired position with respect to the loader 20. A lateral support 94 is formed in each side wall 84 and 86 for receiving the rim 72 and restricting the lateral movement of the rim 72. An inner lip 95 is formed in each side wall 84 and 86 for restricting the horizontal movement of the inner surface 68 by engaging the rim 72. A lower support 96 is formed between the side walls 84 and 86 to support the cassette 50 in the main carriage 78. An outlet support lip 98 is formed at the lower end of outer opening 90 to fit around and restrict the movement of the cassette outlet 54.

The front carriage assembly 74 includes left and right front fascia 102 and 104 that hold the main carriage 78 and attach the main carriage 78 to the rest of the loader 20. Each front fascia 102 and 104 has a main body 106 with a side opening 108 for receiving the main carriage 78 therein.

With reference to FIGS. 5, 6 and 8, the front fascia 102 and 104 form openings which correspond to matching openings in the main carriage 78. Thus the front fascia 102 and 104 has outer opening 114, inner opening 116, and defines the top opening 76. The outer opening 114 adjoins the outer opening 90 of the main carriage 78 and permits a user to see that a cassette 50 is contained within the front carriage assembly 74. A tube support opening 115 is formed at the lower end of outer opening 114 to fit around and restrict the movement of the tube support 58. The inner opening 116 adjoins open base surface 82 and permits access to the inner surface 68 of the cassette 50.

Figure 9:
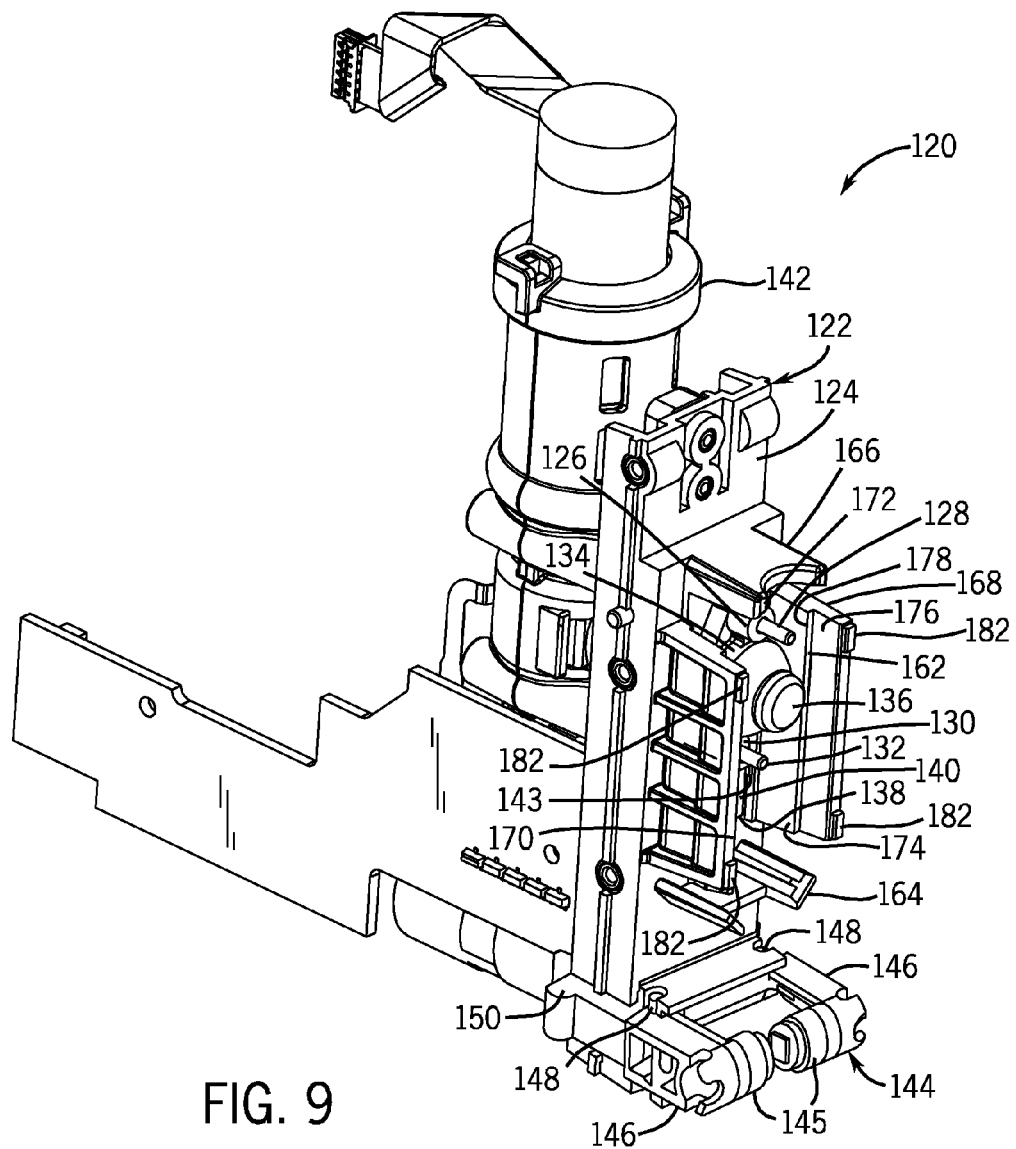
FIG. 9 is a perspective left side view of the pump chassis assembly.

With reference to FIG. 9, a pump chassis assembly 120 is shown. The pump chassis assembly 120 has a main chassis 122 with a vertically disposed base surface 124. The base surface 124 has an opening 126 permitting an inlet pressure sensor 128 to pass through the base surface 124 and extend horizontally therefrom. An opening 130 in the base surface 124 is positioned below the inlet pressure sensor 128 and permits an outlet pressure sensor 132 to pass through the base surface 124 and extend horizontally therefrom. An opening 134 in the base surface 124 is positioned between the inlet pressure sensor 128 to and the outlet pressure sensor 132 and permits a plunger 136 to pass through the base surface 124 and extend horizontally therefrom. A motor 142 is connected to the plunger 136 for driving (or reciprocating) the plunger back and forth.

An opening 138 in the base surface 124 is positioned below the outlet pressure sensor 132 and permits an orientation sensor 140 to pass through the base surface 124 and be positioned flush with the base surface 124. The orientation sensor 140 is shown as an infrared reflective sensor which determines the distance to the cassette 50. The orientation sensor 140 is located to detect the presence or absence of flow stop 70 as an irregular portion of the inner surface 68. The detection of the presence or absence of flow stop 70 is used to align the cassette 50 as well as monitor the orientation of the cassette 50.

Figure 13:
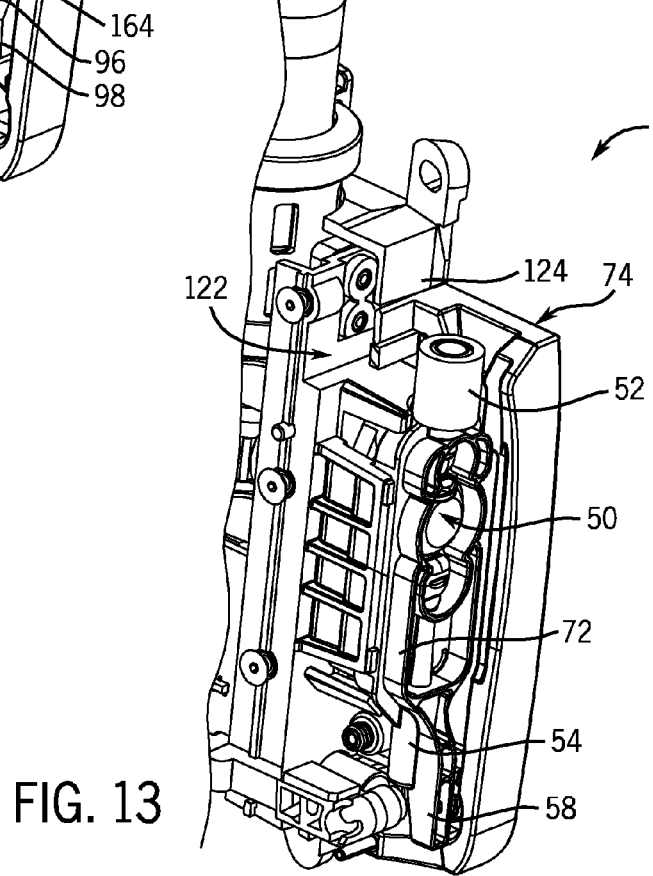
FIG. 13 is a partial sectional left side perspective view similar to FIG. 12, but a cassette is in the closed loader.

With reference to FIGS. 5, 9 and 13, once a cassette 50 is fully loaded and the front carriage assembly 74 is closed, the inlet pressure sensor 128 engages the inlet diaphragm 62 of cassette 50. The outlet pressure sensor 132 engages the outlet diaphragm 64. The plunger 136 engages the pumping chamber 66. A flow stop post 143 positioned between the outlet pressure sensor 132 and the orientation sensor 140 on the base surface 124 engages and closes the flow stop 70 by forcing the flow stop 70 to a closed position. The flow stop post 143 prevents free flow of fluid through cassette 50 once the front carriage assembly 74 is closed.

With reference to FIGS. 8 and 9, one embodiment of the present invention is shown with a pair of air sensors 144 including sensor heads 145 attached to the near ends of arms 146. The arms 146 are pivotally secured to the base surface 124 at hinge 148. The arms 146 are spring biased to pull the air sensors 144 together. A cam element 150 extends horizontally from the far end of each arm 146.

An air sensor slot 152 is formed in each front fascia 102 and 104 to receive the near ends of arms 146 as the front carriage assembly 74 moves in and out with respect to the main chassis 122. Air cam plates 154 extend horizontally from each front fascia 102 and 104 to engage and drive the cam elements 150 of the air sensors 144.

When the front carriage assembly 74 is fully extended, an open portion 156 of each air cam plate 154 forces the cam elements 150 inward, pivoting the arms 146 about the hinges 148 and moving the sensor heads 145 apart. When the front carriage assembly 74 is fully withdrawn, a closed portion 158 of each air cam plate 154 allows the spring biased cam elements 150 to move outward, pivoting the arms 146 about the hinges 148 and moving the sensor heads 145 together. A ramp portion 160 of each air cam plate 154 is located between the open portion 156 and the closed portion 158 of each air cam plate 154 for providing a smooth transition for the cam element 150 as it moves from the open portion 156 to the closed portion 158.

The outward movement of the sensor heads 145 is required to allow effluent tubing (not shown) attached to the cassette outlet 54 to be received between the sensor heads 145. The inward movement of the sensor heads 145 is required to press the sensor heads 145 together to squeeze the effluent tubing (not shown). This squeezing is necessary for the sensor heads 145 physically contact the effluent tubing (not shown) to get accurate measurements of air contained therein.

Figure 12:
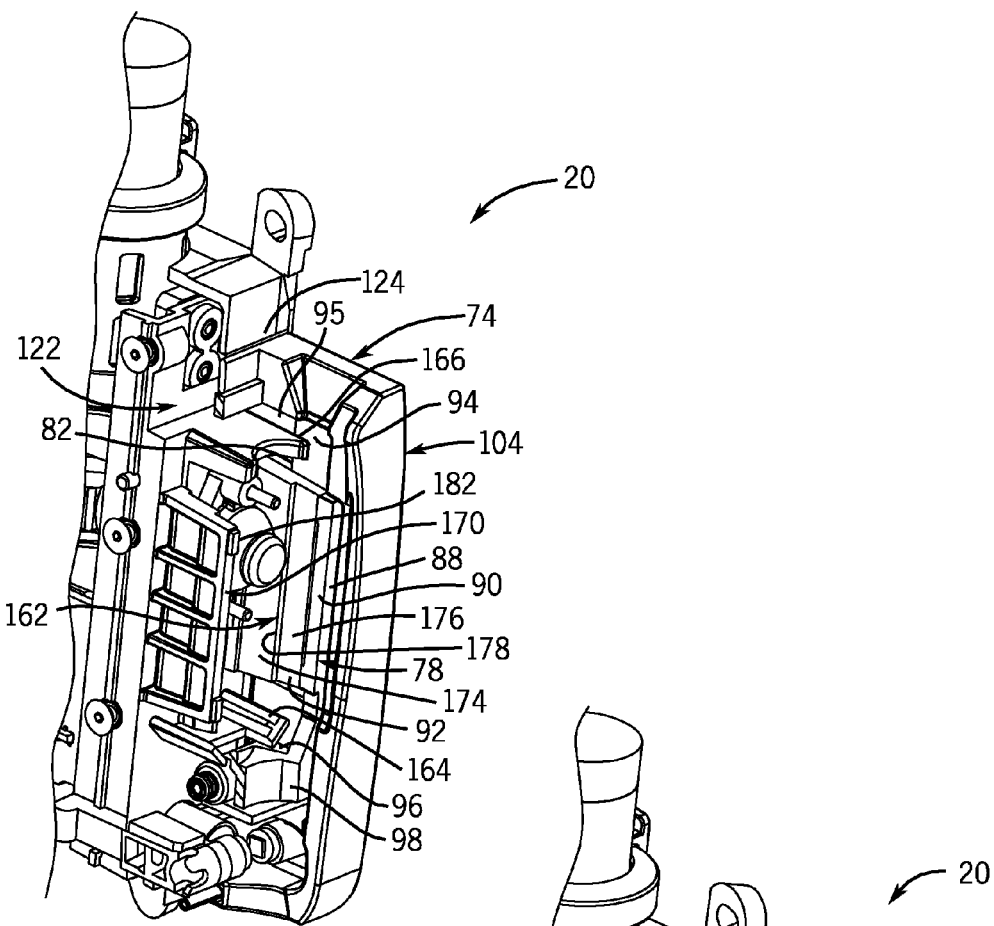
FIG. 12 is a partial sectional left side perspective view of a closed loader with no cassette taken along line 12-12 in FIG. 7, where the left slide assembly is removed and the carriage is in vertical cross section.

With reference to FIGS. 8, 9 and 12, a fixed seat 162 is formed by multiple finger elements 164, 166, 168, and 170 extending horizontally from the vertical base surface 124. The bottom finger element 164 is positioned below the orientation sensor 140 and receives the cassette outlet 54 to restrict the movement of the inlet 54. The top finger element 166 is positioned above the inlet pressure sensor 128 and has an outer end with a groove 172 therein to receive and restrict the movement of the inlet 52. Left and right lateral finger elements 168 and 170 are positioned on either side of the plunger 136.

The top, right and left finger elements 166, 168, and 170 have a finger base 174 attached to the vertical base surface 124, a finger tip 176 extending horizontally from the finger base 174 toward the main carriage 78, and an end stop ledge 178 formed between the finger base 174 and the finger tip 176. Each finger tip 176 being tapered with a narrowed portion facing the main carriage.

Corresponding finger grooves 180 are formed in each side wall 84, 86 for receiving the left and right lateral finger elements 168, 170, respectively, of the main chassis 122. Each groove 180 has a closed end formed by the outer lips 88 for abutting corresponding finger posts 182 formed at outer ends of the finger tips 176.

Figure 10:
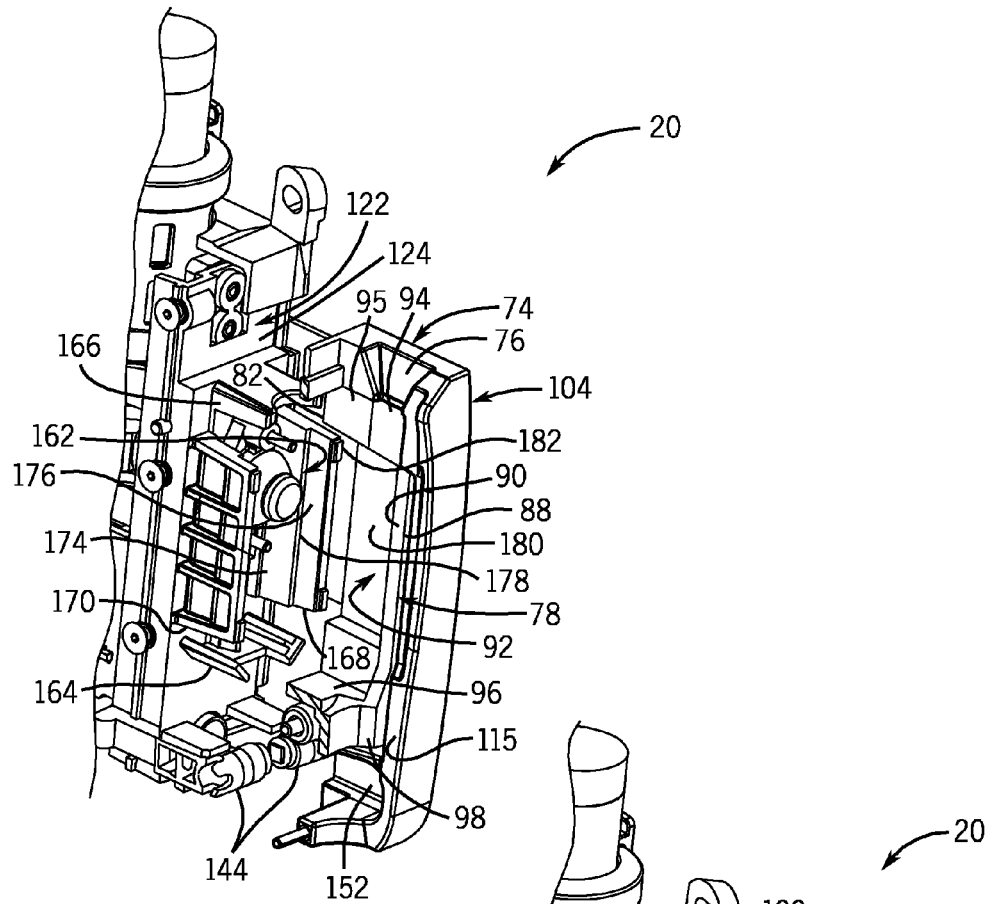
FIG. 10 is a partial sectional left side perspective view of an open loader with no cassette taken along line 10-10 in FIG. 6, where the left slide assembly is removed and the carriage is in vertical cross section.
Figure 11:
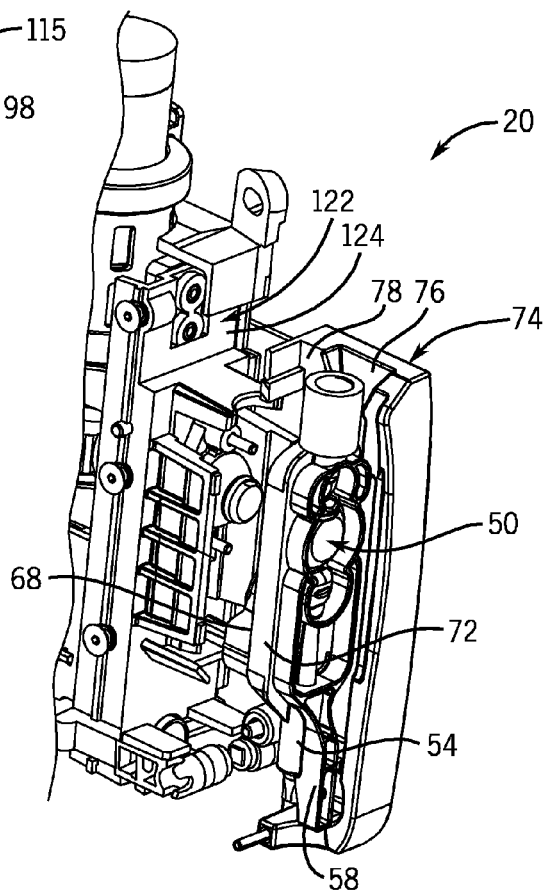
FIG. 11 is a partial sectional left side perspective view similar to FIG. 10, but a cassette is in the open loader.

With reference to FIGS. 10 and 11, in operation the cassette 50 is inserted into top opening 76 of the front carriage assembly 74, when the loader 20 is in the open position. Upon insertion, the cassette 50 slides into the main carriage 78 and is loosely secured in place by cassette footing 92. The lateral support 94 of the cassette footing 92 restricts the lateral movement of the cassette rim 72; the inner lip 95 and the outlet support lip 98 restrict the horizontal movement of the cassette inner surface 68 by engaging the rim 72; and the outlet support lip 98 fits around and restricts the movement of the cassette outlet 54.

With reference to FIGS. 10, 12 and 13, the main carriage 78 is movable from an open position horizontally inwardly with respect to the main chassis 122 to a closed position to engage the cassette 50 to the fixed seat 162. When the loader 20 is loaded with a cassette 50 and closed, the left and right lateral finger elements 168, 170 are received within the finger grooves 180 between the side walls 84, 86 and the cassette 50. The cassette footing 92 permits the cassette 50 to adjust its position within the main carriage 78 while the cassette 50 is being forced onto the fixed seat 162.

Figure 14:
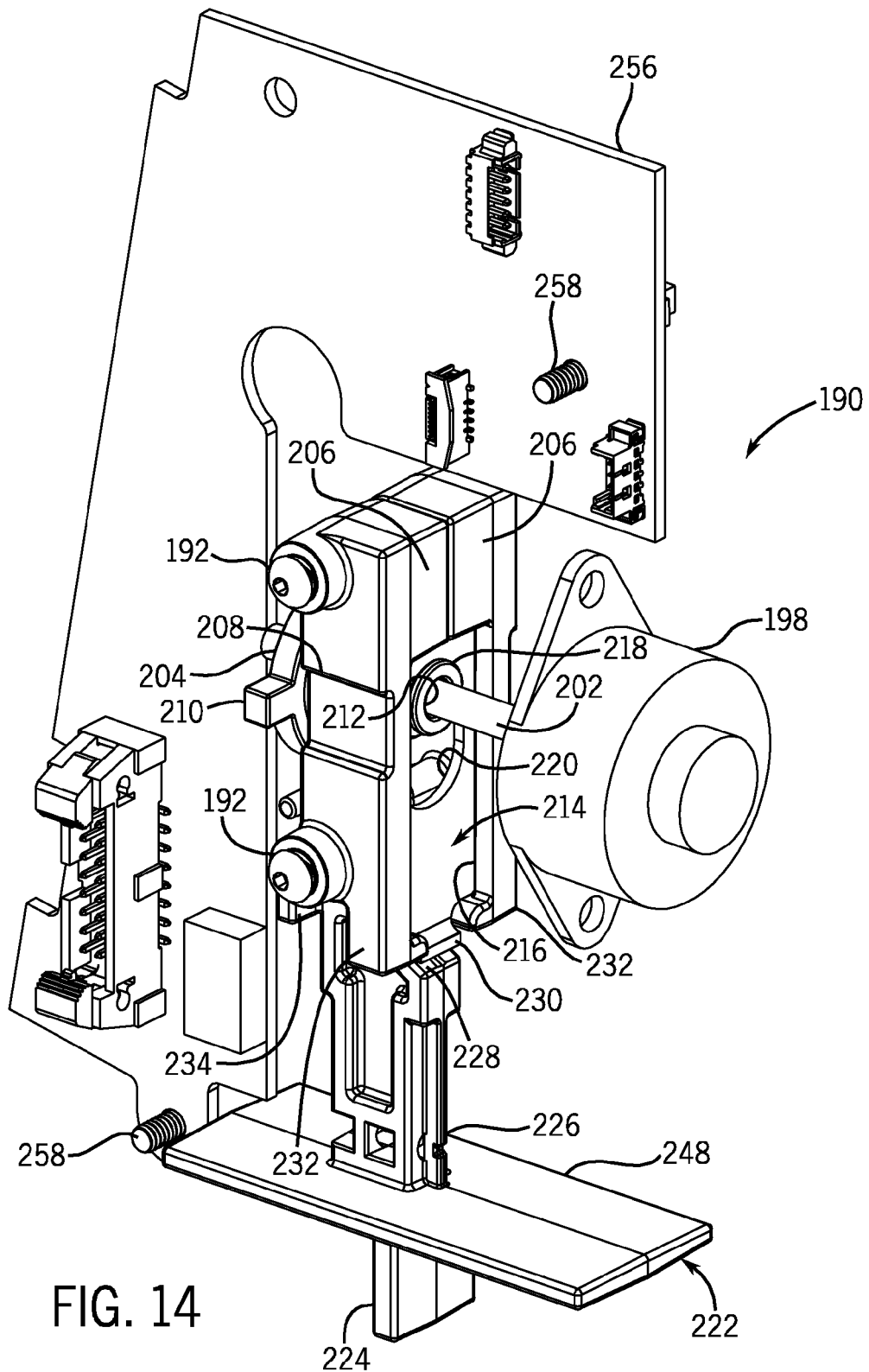
FIG. 14 is a perspective left side view of a manual release, actuator assembly and infuser board.

With reference to FIGS. 8 and 14, a rear carriage assembly 190 has fasteners 192 to connect to fastener receivers 194 formed in side plates 196 of the front carriage assembly 74. Each side plate 196 extends from one of the front fascia 102, 104 towards the rear carriage assembly 190. A clearance opening 195 is formed through each of the side plates 196 and a curved notch 197A is formed in each main body 106 for receiving a corresponding curved post 197B which extends horizontally from each of the side walls 84 and 86 of the main carriage 78. The sets of curved notches 197A and posts 197B allow minor movement of the main carriage 78 within the side openings 108 of the front fascia 102 and 104.

With reference to FIGS. 5, 8 and 10, additionally, the curved posts 197B allow the main carriage 78 to "float" with respect to the main chassis 122. This floating of the main carriage 78 allows the fixed seat 162 to dictate the position of both the main carriage 78 and cassette 50 when the main carriage 78 is in the closed position. Thus the main carriage 78 has rotational freedom on at least one axis with respect to the main chassis 122.

While the embodiment described above is directed to rotational freedom on at least one axis, one of ordinary skill in the art will appreciate that various embodiments that permit rotational freedom on two or even three axes may be provided without departing from the present invention. For instance, it is contemplated that the main carriage 78 could be attached to a gimbal system (not shown) which would allow full XYZ rotational freedom to the main carriage 78 with respect to the main chassis 122.

The finger elements 164, 166, 168, and 170 of the fixed seat 162 dictate the vertical and lateral position of the cassette 50, while the carriage 78 is held against posts 182. Posts 182 are the defining features for the inward/outward location of the cassette 50. The lips 88 of the main carriage 78 contact the posts 182 and the rim 72 of the cassette 50 simultaneously, controlling their registration.

The rim 72 and posts 182 are both in contact with the same surface of the main carriage 78, and therefore are coincident with each other.

One of ordinary skill in the art will appreciate that various embodiments of the finger elements 164, 166, 168, and 170 may be provided without departing from the present invention. For instance, finger element 164 may be provided as a flexible resilient member to provide an upward biasing force on the cassette 50 while also displacing to accommodate some variance in the positioning of the cassette 50. Similarly, finger element 166 may be a flexible resilient member to provide a downward biasing force.

With reference to FIGS. 8 and 14, the rear carriage assembly 190 includes an actuator 198 connected to the main carriage 78 via the side plates 196 to automatically move the main carriage 78 from the open position to the closed position. The actuator 198 is shown as a linear actuator; however other types of drives may be used without departing from the present invention. For instance, a cam plate driven by a DC motor could be used instead of the linear actuator 198 shown here.

Figure 16:
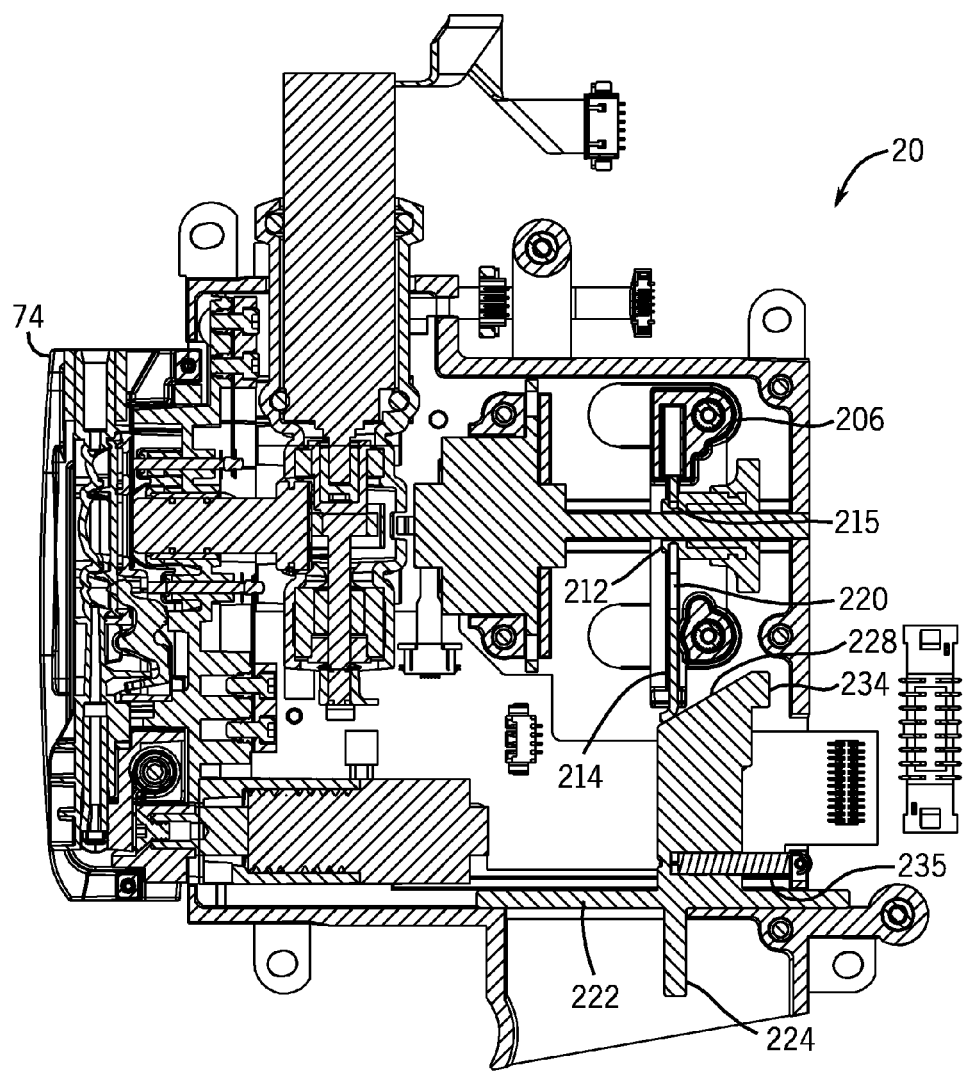
FIG. 16 is a vertical cross sectional side view of the loader in the closed position with a cassette loaded in it.

With reference to FIGS. 14 and 16, a threaded shaft 202 is driven by the actuator 198. As the shaft 202 turns, a nut 204 is tightened or loosened along the length of the shaft 202 (i.e. moves axially). This tightening or loosening of the nut 204 transfers the rotational drive of the actuator 198 into a linear motion to drive the front carriage assembly 74. Left and right plate housings 206 are positioned around the nut 204 and contain a slot 208 which receives a pin element 210 of the nut 204. An adapter 212 is located on the shaft 202 to attach the nut 204 to the plate housing 206. A release plate 214 is downwardly biased (i.e. by gravity, spring, or other device) and slidably received within a vertical plate slot 216 formed in the plate housing 206. An engagement portion 218 is formed as a hole in the release plate 214 for normally coupling and slidably engaging the release plate 214 to an annular groove 215 on the nut adapter 212.

In an emergency, the release plate 214 can be manually uncoupled or disengaged from the nut adapter 212, thus disengaging the actuator 198 from the front carriage assembly 74. A release aperture 220 is formed as a hole in the release plate 214 and is positioned below but connected to the engagement portion 218. The release aperture 220 has a greater diameter than the engagement portion 218. Preferably the release aperture 220 and the engagement portion 218 partially overlap, with the engagement portion 218 having a diameter slightly larger than the groove 215 and the release aperture 220 having a clearance diameter significantly larger than the nut adapter 212 adjacent to the groove 215. As the release plate 214 is raised, the engagement portion 218 is raised out of the groove 215 in the nut adapter 212 and the release aperture 220 allows the release plate 214 to be slid over the nut adapter 212, thereby uncoupling or disengaging the plate housing 206 and front carriage assembly 74 from the actuator 198.

An emergency release element 222 is provided for raising the release plate 214 and disengaging the plate housing 206 from the actuator 198. The emergency release element 222 has a finger switch 224 allowing a user to manually pull forward the spring biased emergency release element 222. The emergency release element 222 allows a user to manually remove cassette 50 from the pump 10 in cases of pump malfunction or loss of power.

Figure 17:
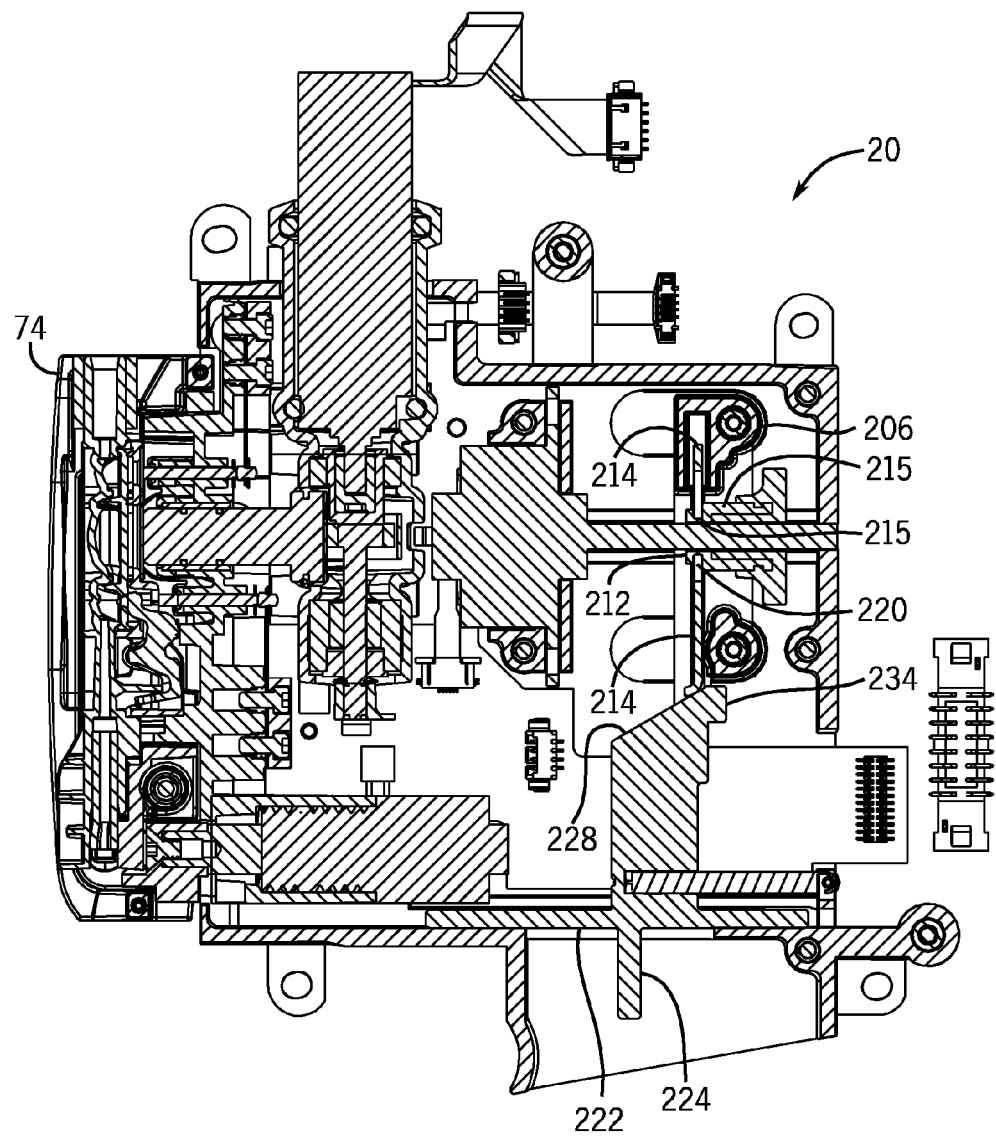
FIG. 17 is a vertical cross sectional side view of the loader having the emergency released engaged with the actuator assembly so that the release plate is raised.

With reference to FIGS. 14 and 17, as the emergency release element 222 moves forward, a vertical column 226 having an upper end forming a ramp 228 engages a bottom edge 230 of the release plate 214. The vertical column 226 passes between lower legs 232 of the plate housing 206, with the ramp 228 gradually raising the release plate 214 until the release aperture 220 is positioned around or aligned with the nut adapter 212. At the apex of the ramp 228, side tabs 234 extending horizontally from the vertical column 226 engage the lower legs of the plate housing 206.

Figure 18:
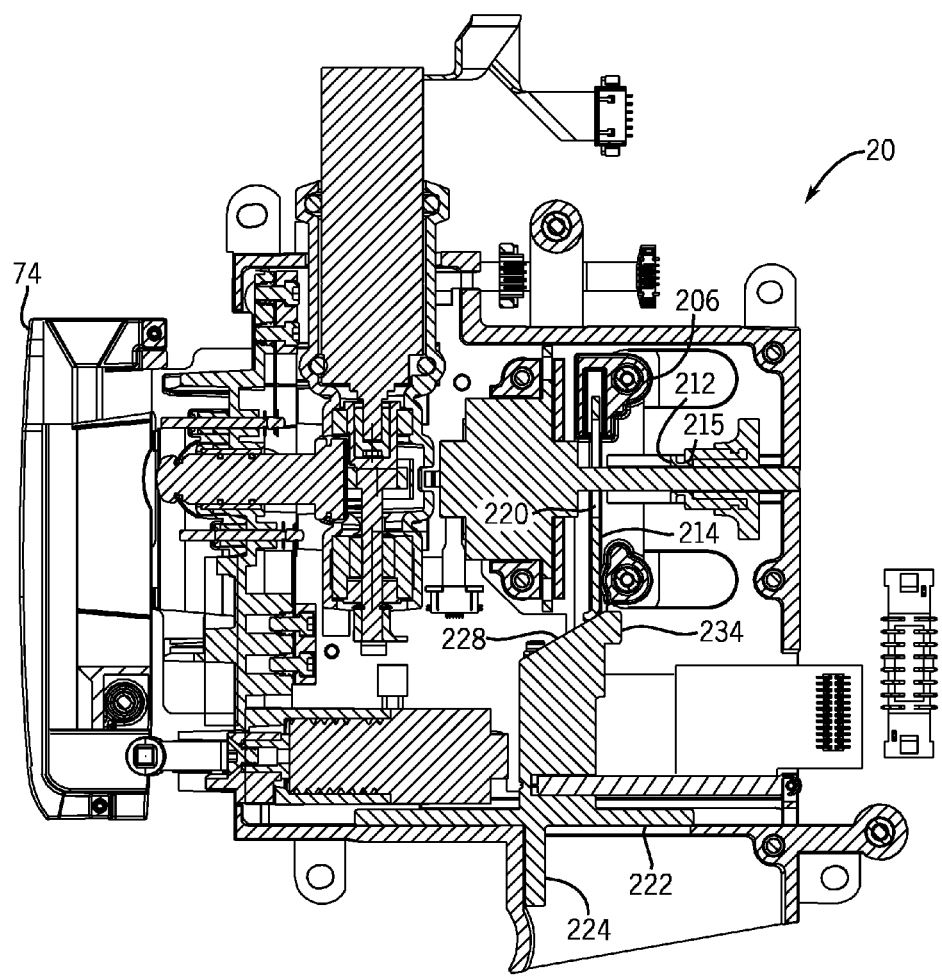
FIG. 18 is a vertical cross sectional side view of the loader where the actuator assembly is disengaged.

With reference to FIG. 18, once the release plate 214 is raised, the forward motion of the emergency release element 222 causes the side tabs 234 to push the plate housing 206 forward. The release aperture 220 is slid over the nut adapter 212, and the plate housing 206 and front carriage assembly 74 are moved to the open position disengaged from the actuator 198.

Figure 19:
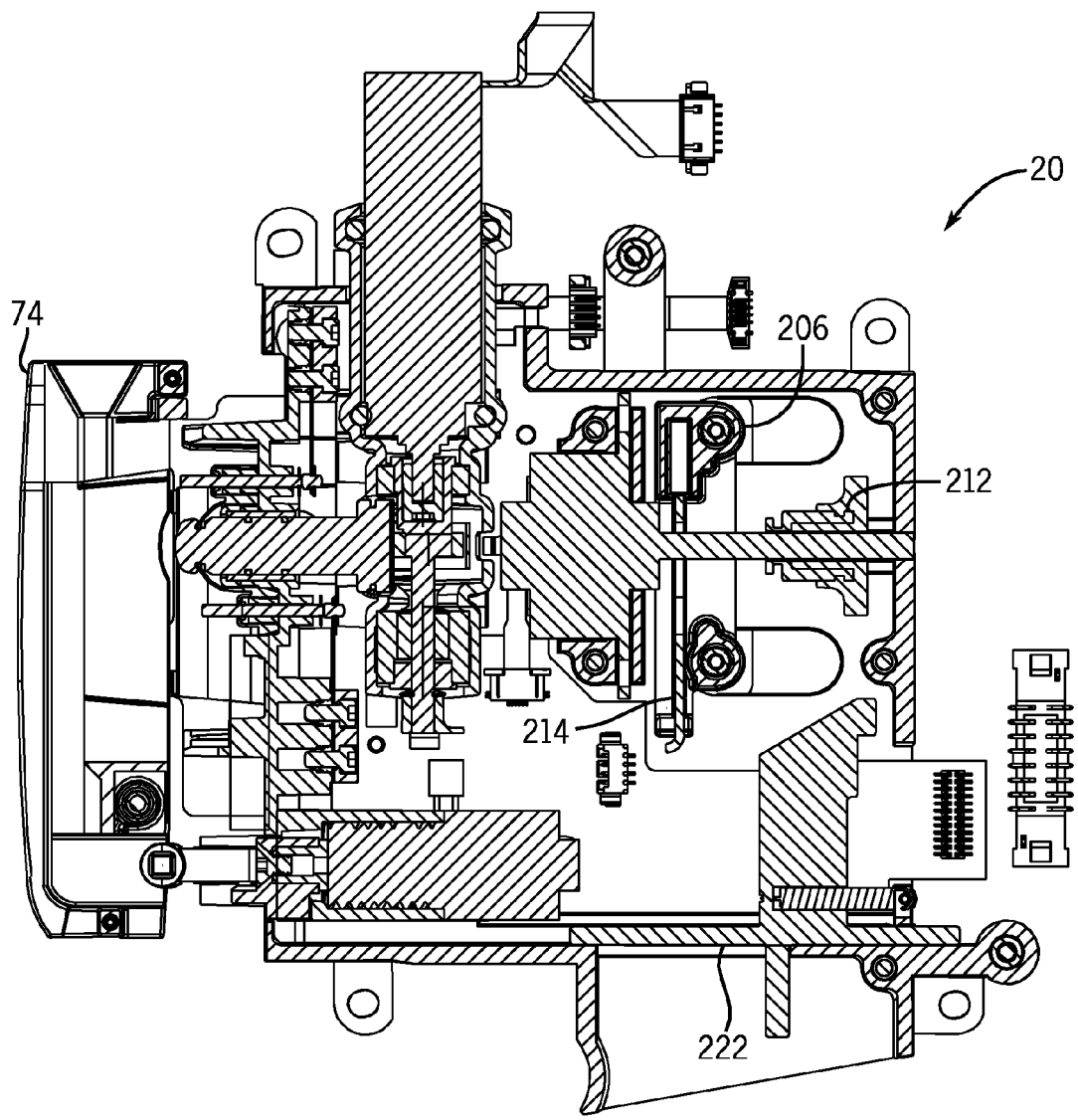
FIG. 19 is a vertical cross sectional side view of the loader where the actuator assembly is disengaged and the manual release is returned to its home position.

With reference to FIGS. 16 and 19, once the user activates the emergency release element 222, it can then be released. A spring 235 (or other biasing device) biases or returns the emergency release element 222 to its normal position, while the plate housing 206 and front carriage assembly 74 remain in the open position and also remain disengaged from the actuator 198. The spring biased release plate 214 lowers itself to rest on the shaft 202. In this position, the release plate 214 cannot be reengaged to the nut adapter 212.

Further, manually pressing the front carriage assembly 74 to a closed position while pulling the emergency release element 222 forward will not reengage the nut adapter 212 as a certain amount of tension between the nut adapter 212 and release plate 214 was released when the emergency release element 222 was originally pulled. This amount of released tension is enough to prevent a user from manually forcing the front carriage assembly 74 back far enough to register the engagement portion 218 of release plate 214 with the groove 215 in the nut adapter 212.

When the actuator 198 originally drove the front carriage assembly 74 to a closed position, the actuator 198 induced the above-mentioned releasable tension by pulling the main carriage 78 hard against the posts 182. The actuator 198 is driven past the point of initial contact until increasing mechanical resistance stalls it or a predetermined electrical load is reached. The nut 204 and nut adapter 212 are driven back as far as possible. In doing so, all of the dimensional slack is taken out of the interconnected chain of components, including but not limited to the main chassis 122, side chassis 236, 238, rear carriage assembly 190 (actuator 198, shaft 202 and nut 204), side plates 196, and main carriage 78. These components are placed under tension or compression, depending on their function, by the pull of the overdriven actuator 198. The user who tries to reengage the nut adapter 212 and release plate 214 would have to manually recreate these conditions in order to reengage. However, the user cannot reach the internal components such as the actuator 198, threaded shaft 202 and nut 204 to establish such conditions.

The prevention of manual reengagement between the nut adapter 212 and release plate 214 provides a continuous visual indicator that the pump 10 is not operational due to the open position of front carriage assembly 74. The prevention of manual reengagement between the adapter 212 and release plate 214 also ensures that error signals generated by pump 10 must be addressed prior to recoupling or reengaging the nut adapter 212 and release plate 214 and restarting the pump 10.

Thus, it can be appreciated that no manual closure of the front carriage assembly 74 is possible with the present invention. By pump 10 requiring the automated closure of front carriage assembly 74, a user is not able to insert a cassette 50 into a non-operational pump 10. This ensures that the full array of detection and safety elements in pump 10 are active when a cassette 50 is engaged with the pump 10.

Figure 20:
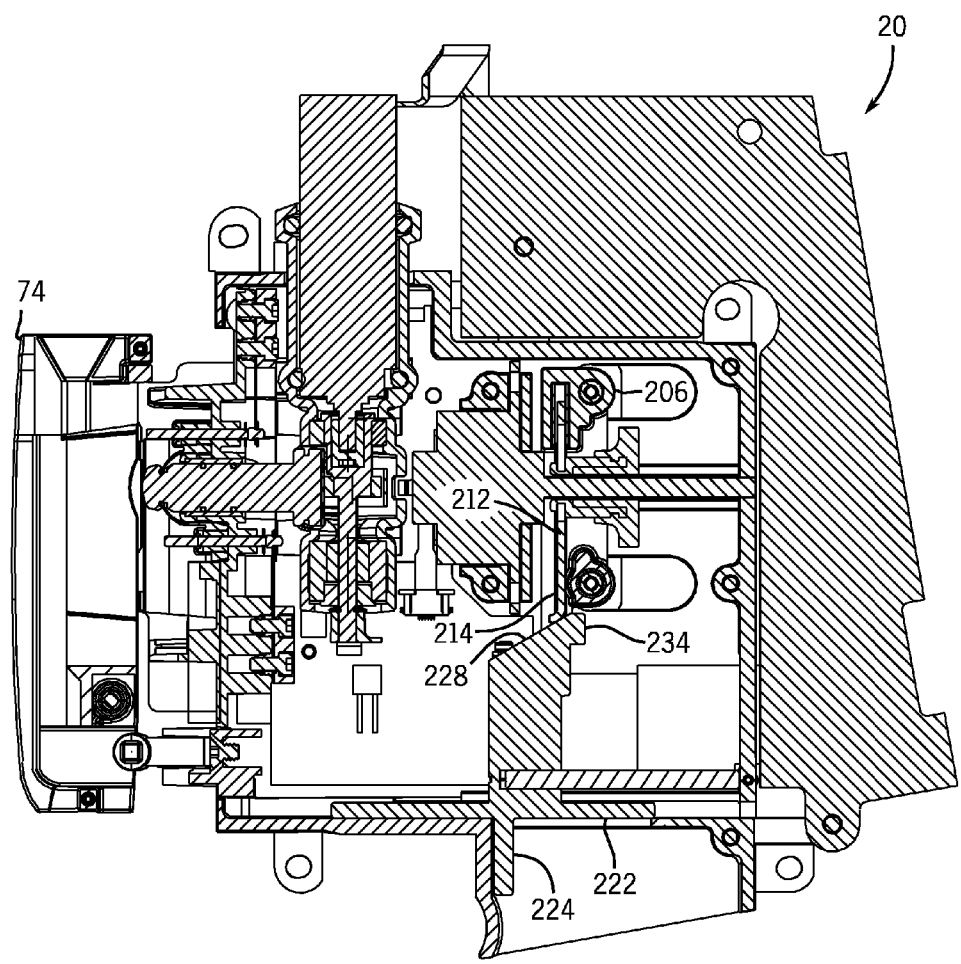
FIG. 20 is a vertical cross sectional side view of the loader where the manual release is pulled forward and the actuator driven forward so that the release plate is raised for reengaging the actuator assembly.

With reference to FIG. 20, to reengage the actuator 198 the user must electrically drive the actuator 198 forward while simultaneously pulling the emergency release element 222 forward. This allows the groove 215 of the nut adapter 212 to be driven underneath the engagement portion 218 of the release element 214. Once the groove 215 of the nut adapter 212 is beneath the engagement portion 218, the emergency release element 222 can be released. When the emergency release element 222 is released, the engagement portion 218 drops into the groove 215 of the nut adapter 212 and reengages the front carriage 74 to the actuator 198.

Figure 15:
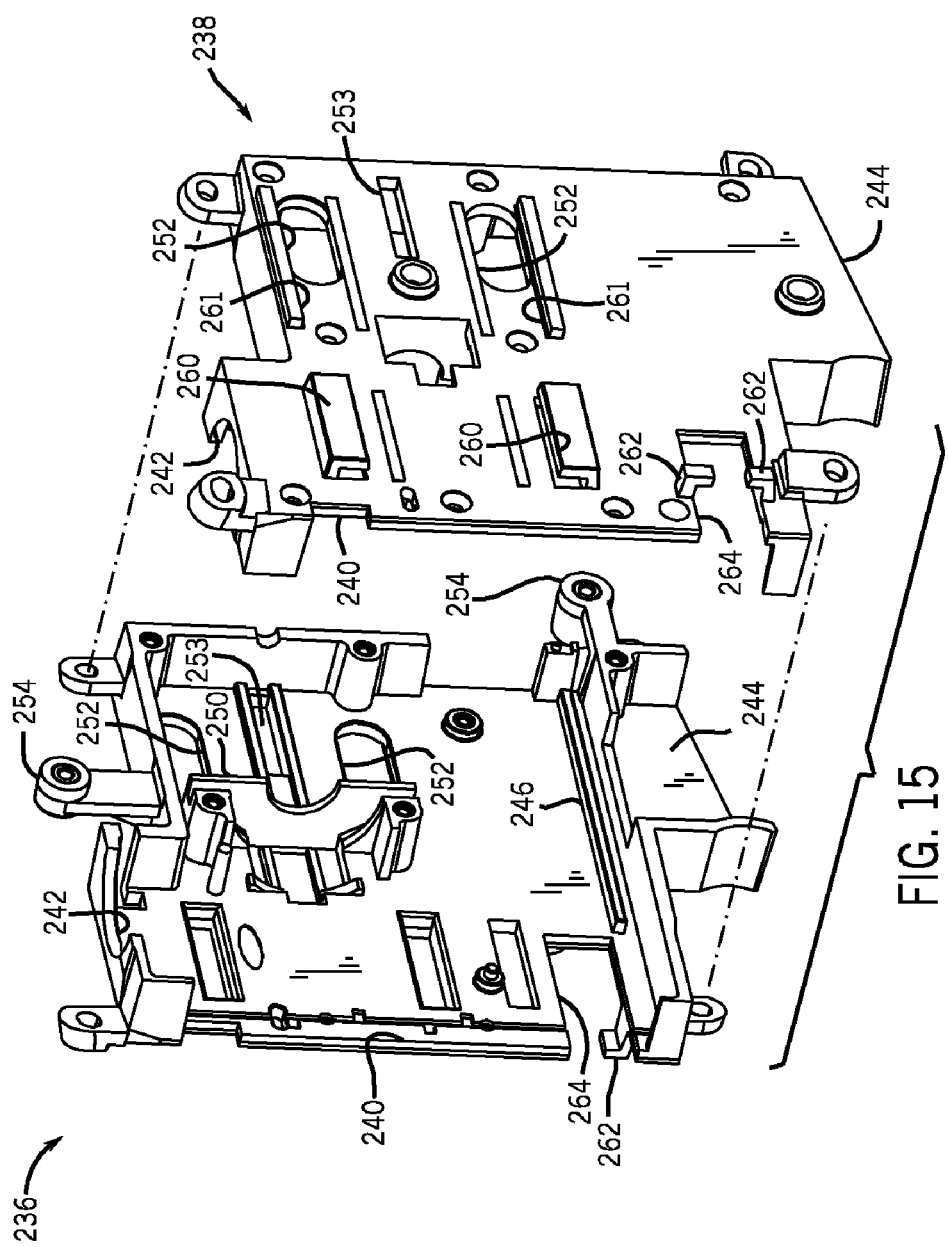
FIG. 15 is an exploded perspective right side view of the left and right chassis substrate.

With reference to FIG. 15, left and right side chassis 236 and 238 house the pump chassis assembly 120 of FIG. 9 and the rear carriage assembly 190 of FIG. 14. A front opening 240 is formed in the side chassis 236 and 238 to fit around the main chassis 122. An upper opening 242 is formed in the side chassis 236 and 238 to fit around the motor 142.

A lower channel 244 is formed in the side chassis 236 and 238 to fit around the manual release finger switch 224. The lower channel 244 surrounds the finger switch 224 and is sealed to the manual release opening 26 of infuser cover 16, allowing a user to access the finger switch 224 from outside the infuser cover 16. A manual release groove 246 slidably receives a horizontally flat plate slider 248 of the emergency release element 222, allowing the emergency release element 222 to slide back and forth along the manual release groove 246.

An actuator seat 250 is formed in the side chassis 236 and 238 to fit around the actuator 198 and secure the actuator to the side chassis 236 and 238. Rear carriage ports 252 are formed in the side chassis 236 and 238 to allow the rear carriage fasteners 192 to pass through the side chassis 236 and 238 to attach the rear carriage assembly 190 to the side plates 196 of the front carriage assembly 74. The rear carriage ports 252 also allow the rear carriage fasteners 192 to move back and forth as the actuator 198 drives the plate housing 206. Nut ports 253 slidably receive the pin elements 210 of the nut 204 and prevent the nut 204 from rotating when actuator 198 is activated.

With reference to FIGS. 6, 14 and 15, female fasteners 254 extend from the outer surface of side chassis 236 and 238 to secure an infuser circuit board 256 via male fasteners 258.

With reference to FIGS. 6, 9 and 15, side plate channels 260 are formed as paired "L" shaped brackets on the outer surface of side chassis 236 and 238. The side plate channels 260 slidably hold the side plates 196 of the front carriage assembly 74 as it moves back and forth. Additionally, side plate guides 261 are formed as paired box shaped bumpers adjacent the rear carriage ports 252 on the outer surface of side chassis 236 and 238. The side plate guides 261 are spaced apart and may be preferably positioned parallel to one another. The side plate guides 261 are positioned on both the top and bottom of the side plates 196 to prevent rotation of the side plates 196 near the rear carriage ports 252. These side plate channels 260 and side plate guides 261 provide for a straight line insertion of the front carriage assembly 74, which avoids the adverse rotational effects of prior art manual loaders.

Air cam channels 262 formed as paired "L" shaped brackets on the outer surface of side chassis 236 and 238. The air cam channels 262 slidably hold the air cam plates 154 of the front carriage assembly 74 as it moves back and forth horizontally. Air cam ports 264 are formed through the side chassis 236 and 238 adjacent the air cam channels 262. The air cam ports 264 permit the cam elements 150 of the air sensors 144 to contact the air cam plates 154.

With reference to FIGS. 6 and 8, a position sensor 266 is attached to the outer surface of the left side chassis 236. The position sensor 266 monitors the position of a slot 268 formed in a position plate 270. The position plate 270 is preferably an integral portion of the left side plate and extends horizontally from the left front fascia 102. Alternatively, the position sensor 266 can monitor the position of an end edge 272 of the position plate 270. By monitoring the position of the position plate 270 the position sensor 266 detects the overall position of the front carriage assembly 74 and the main carriage 78. The position sensor 266 shown is a linear pixel array sensor that continuously tracks the position of the slot 268, and does not merely indicate when the slot 268 has passed a fixed point. It will be understood that other devices can be used for the position sensor 266, such as an opto-tachometer sensor.

Figure 21:
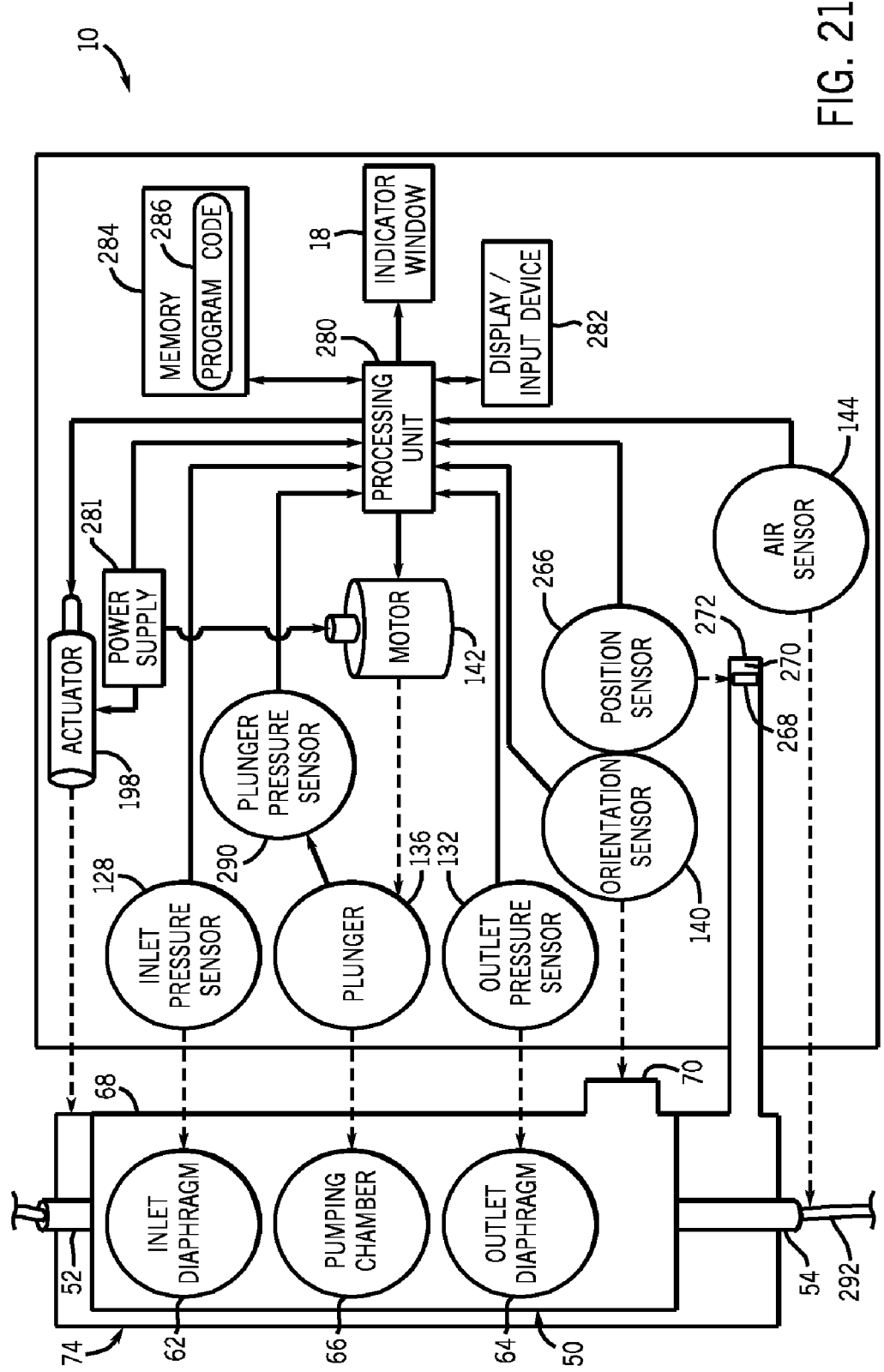
FIG. 21 is a schematic diagram of the medical pump of the present invention, illustrating the functional components of the pump and the cassette.

FIG. 21 is a schematic diagram illustrating the functional components of the medical pump 10 used in connection with the disposable cassette 50 for delivering a fluid to a patient. A processing unit 280 is included in pump 10 and performs various operations described in greater detail below.

The processing unit 280 is powered by a power supply 281. The processing unit 280 controls the electric motor 142 being energized by the power supply 281. When energized, the electric motor 142 causes the plunger 136 to reciprocate back and forth to periodically down-stroke, causing plunger 136 to press on pumping chamber 66, driving fluid through cassette 50. On an up-stroke, plunger 136 releases pressure from pumping chamber 66 and thereby draws fluid from inlet 52 into pumping chamber 66.

Likewise the processing unit 280 controls the actuator 198 being energized by power supply 281. When energized, the actuator 198 drives the front carriage assembly 74 to closed or open positions.

A memory 284 communicates with the processing unit 280 and stores program code 286 and data necessary for the processing unit 280 to calculate and output the operating conditions of pump 10. The processing unit 280 retrieves the program code 286 from memory 284 and applies it to the data received from various sensors and devices of pump 10, as will be described in more detail below.

The processing unit 280 processes the data from pump 10 to determine all of the following operating conditions: the cassette 50 is incorrectly oriented, where there is no cassette 50 at all, where the cassette 50 is not fully seated to the fixed seat 162, when the front carriage assembly 74 is in an open or closed position, when a jam in the front carriage assembly 74 is detected, when there is proper flow of fluid through the cassette 50 to the patient, and if air bubbles are entrained in the fluid leaving cassette 50. Once the operating condition has been determined, the processing unit 280 can output the operating condition to display 282, activate indicator window 18, and/or use the determined operating condition to adjust operation of the pump 10.

Specifically, processing unit 280 receives data from a plunger pressure sensor 290 operatively associated with the plunger 136. The plunger pressure sensor 290 senses the force on plunger 136 and generates a pressure signal based on this force. The plunger pressure sensor 290 communicates with the processing unit 280, sending the pressure signal to the processing unit 280 for use in determining operating conditions of pump 10.

The processing unit 280 receives an array of pressure data sensed from the cassette inner surface 68 determined by the plunger pressure sensor 290 and inlet and outlet pressure sensors 128 and 132. The processor 280 combines the pressure data from the plunger pressure sensor 290 with data from inlet and outlet pressure sensors 128 and 132 to provide one determination as to the correct or incorrect positioning of cassette 50. In normal operation, this array of pressure data falls within an expected range and the processing unit 280 determines that proper cassette loading has occurred. Where the cassette 50 is incorrectly oriented (backwards or upside down, for instance) or where the cassette 50 is not fully seated to the fixed seat 162, the array of pressure data falls outside the expected range and the processing unit 280 determines that improper cassette loading has occurred.

Further, once the cassette 50 is fully seated correctly and pumping operation begins, the array of pressure data is analyzed by the processing unit 280 to determine proper flow of fluid through the cassette 50 to the patient. In one use, the processing unit 280 uses this pressure signal from plunger pressure sensor 290 to determine that the cassette is properly pressing on the plunger 136 and activates the plunger 136 to begin pumping the cassette 50. In another use, the processing unit 280 uses this pressure signal from inlet pressure sensor 128 to determine if fluid is being supplied to the cassette 50. In a further use, the processing unit 280 uses this pressure signal from outlet pressure sensor 132 to determine the overall fluid pressure being delivered to the patient.

Similarly, the processing unit 280 determines the orientation and presence of cassette 50 by processing data received from the orientation sensor 140. The detection of the presence or absence of flow stop 70 is used to align the cassette 50 as well as monitor the orientation of the cassette 50. In normal operation, this distance data falls within an expected range for the distance between the orientation sensor and flow stop 70, and the processing unit 280 determines that proper cassette loading has occurred. Where the cassette 50 is incorrectly oriented (backwards or upside down, for instance), where there is no cassette at all, or where the cassette 50 is not fully seated to the fixed seat 162, the distance data falls outside the expected range and the processing unit 280 determines that improper proper cassette loading has occurred.

Additionally, once the processing unit 280 processes data received from the orientation sensor 140 to determine the presence of a properly loaded cassette 50 in open front carriage assembly 74, the processing unit 280 will automatically close front carriage assembly 74 after a given period of time and without a direct user command. This timed closure of front carriage assembly 74 prevents free flow of fluid through the cassette 50 as the flow stop post 143 engages and closes the flow stop 70 by forcing the flow stop 70 to a closed position, once the front carriage assembly 74 is closed.

Further, the processing unit 280 can process data received from the orientation sensor 140 to determine if the flow stop 70 is in an open or closed position, once the cassette 50 is inserted into open front carriage assembly 74. If the processing unit 280 determines that the flow stop 70 is in an open position creating free flow, the processing unit 280 can generate an alarm and/or automatically close front carriage assembly 74 after a given period of time and without a direct user command. This prevents free flow of fluid through the cassette 50 as the flow stop post 143 engages and closes the flow stop 70, once the front carriage assembly 74 is closed.

The processing unit 280 also receives data from air sensors 144 pressed to effluent tubing 292 attached to the cassette outlet 54. When squeezed, the air sensors 144 physically contact the effluent tubing 292, the air sensors 144 then excite the effluent tubing 292 with ultrasonic waves to get accurate air content data of air contained therein. In normal operation, this air content data falls within an expected range, and the processing unit 280 determines that proper fluid flow is in progress. When the air content data falls outside the expected range, the processing unit 280 determines and indicates that improper air content is being delivered to the patient.

The position sensor 266 continuously tracks the position of the slot 268 (or end edge 272) portion of the position plate 270. By monitoring the position of the position plate 270 the position sensor 266 detects the overall position of the front carriage assembly 74. The processing unit 280 is connected to the position sensor 266 to receive position data from the position sensor 266. The position data is used by the processing unit 280 to determine when the front carriage assembly 74 is in an open or closed position.

In addition to the position data, the processing unit 280 is also connected to the actuator 198 via power supply 281 to receive electrical load data from the actuator 198. The processing unit 280 combines both the position data and electrical load data to detect jam conditions in the medical pump 10. In normal operation, the electrical load data spikes while the position sensor 266 senses the front carriage assembly 74 in a fully closed position. This spike in the electrical load data is due to the actuator 198 being designed to drive past the closed position. In normal operation this spike in the electrical load data only occurs while the position sensor 266 senses the front carriage assembly 74 in a fully closed position, and the processing unit 280 determines that proper cassette loading has occurred. Where a foreign object (such as a finger or hand) is inserted between the front carriage assembly 74 and the main chassis 122, the spike in the electrical load data occurs prior to the position sensor 266 sensing the front carriage assembly 74 in a fully closed position, and the processing unit 280 determines that that jam conditions have occurred. Additionally, when the processing unit 280 determines that jam conditions have occurred, the processing unit 280 reverses the actuator 198 to open the front carriage assembly 74.

As discussed above, the processing unit 280 receives various data necessary for the processing unit 280 to calculate and output the operating conditions of pump 10. The processing unit 280 retrieves the program code 286 from memory 284 and applies it to the data received from various sensors and devices of pump 10, and generates output. This output is communicated to the user by the processing unit 280 activating the indicator window 18 and/or a display/input device 282.

Specifically, the processing unit 280 activates the light assembly 32 of the indicator window 18 to illuminate the main carriage 78 or to illuminate the outer surface 34 providing visual output information of the pump status to the user. For instance, the processing unit 280 activates the indicator elements 42, to continuously or intermittently light up the outer surface 34 of the window unit 18 with various colors. The coloring and/or flashing is used to provide an indication of the operation conditions of the pump 10. For instance, no lighting would indicate that the pump 10 is off; blue flashing indicates the loader 20 is being opened to load a cassette; continuous blue lighting indicates the cassette is inserted into the loader 20 properly; yellow lighting indicates the cassette is loaded improperly; green lighting indicates normal operation once the cassette is loaded and the pump 10 is running; yellow, orange, and/or red lighting indicates various kinds of abnormal operation once the cassette is loaded and the pump 10 is running. Of course, other condition-indicating color schemes are possible without detracting from the invention.

Additionally, the processing unit 280 activates the light assembly 32 of the indicator window 18 to illuminate the main carriage 78. When processing unit 280 determines that the loader 20 is opened for insertion of a cassette, the illumination elements 46 are activated to illuminate the area where the cassette is inserted into the pump 10. The processing unit 280 may immediately activate the illumination elements 46 or the processing unit 280 may gradually brighten the illumination elements 46 upon opening of the loader 20.

Likewise, the processing unit 280 communicates with the display/input device 282 and allows the user to receive output from processing unit 280 and/or input (data or commands) into the processing unit 280. When the cassette 50 is loaded into the open front carriage assembly 74, a user accesses the display/input device 282 to command the pump 10 to automatically close the front carriage assembly 74. Likewise, a user accesses the display/input device 282 to command the pump 10 to automatically open the front carriage assembly 74 when the cassette 50 is to be removed and/or replaced.

Those of ordinary skill in the art will appreciate that display/input device 282 may be provided as a separate display device and a separate input device. Additionally or multiple separate display devices and/or multiple separate input devices may be provided. For example, as shown in FIG. 1, the medical pump 10 includes a separate load/eject button 283 adjacent the display/input device 282 for commanding the pump 10 to automatically close the front carriage assembly 74 or to automatically open the front carriage assembly 74 when the cassette 50 is to be removed and/or replaced. The separate load/eject button 283 may be located on the infuser mechanism 14 or any other convenient location on the pump 10.

Figure 22:
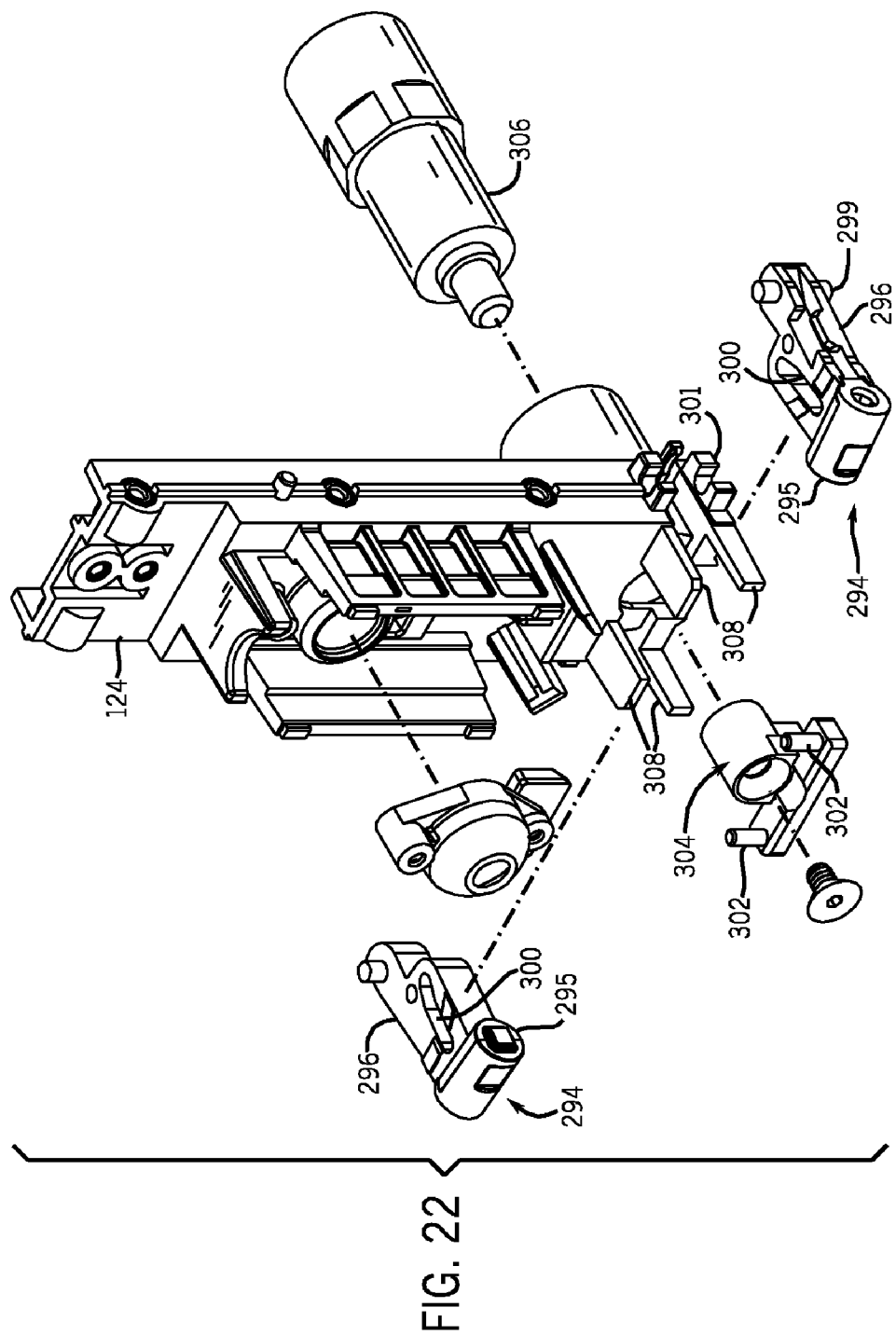
FIG. 22 is a perspective exploded left side view of another embodiment of the front carriage assembly of the present invention.

With reference to FIG. 22, another embodiment of the present invention is shown with a pair of air sensors 294 including sensor heads 295 attached to the near ends of arms 296. The arms 296 are pivotally secured to the base surface 124 at hinge 298, which comprises pin member 299 and a socket 301 for pivotally receiving the pin member 299. The arms 296 each have a cam slot 300 formed therein that receive cam posts 302 located on air sensor cam 304. An air sensor actuator 306 is associated with the air sensor cam 304 to open and close the air sensors 294. Guide elements 308 extend from the base surface 124 to guide the movement of both the arms 296 and the air sensor cam 304.

When the front carriage assembly 74 is traveling to an open position, the processing unit 280 (not shown) activates the air sensor actuator 306 (via power supply 281 not shown) to force the air sensor cam 304 inward, pivoting the arms 296 about the hinges 298 and moving the sensor heads 295 apart. When the front carriage assembly 74 is traveling to a closed position, the processing unit 280 (not shown) activates the air sensor actuator 306 to force the air sensor cam 304 to move outward, pivoting the arms 296 about the hinges 298 and moving the sensor heads 295 together. The cam slots 300 are designed to include: a rapid travel zone where the cam slot 300 profile is such that the arms 296 close rapidly until the touch the effluent tubing 292 (not shown); a compression zone where the cam slot 300 profile is such that the arms 296 are gradually compressed; and a "dwell" zone where the cam slot 300 profile is straight and the arms 296 do not close further with additional air sensor cam 304 motion.

It will be appreciated that carriage loading, orientation sensing and air sensing aspects of the present invention are applicable to other types of medical pumps, including but not limited to syringe pumps, reciprocating plunger pumps and peristaltic pumps. For example, the carriage loader can automatically load a syringe or section of tubing and the air sensors 294 can sense air present in the syringe, tubing connected thereto, or a section of tubing not associate with a syringe.

Whereas the invention has been shown and described in connection with the embodiments thereof, it will be understood that many modifications, substitutions, and additions may be made which are within the intended broad scope of the following claims. From the foregoing, it can be seen that the present invention accomplishes at least all of the stated objectives.

What is claimed is:

1. A medical pump for use with a cassette, comprising:

a main chassis having a fixed seat thereon;

a main carriage connected to the main chassis and having an opening therein adapted to receive a cassette, the opening forming a footing which restricts movement of the cassette within the main carriage;

wherein when the cassette is restricted against movement within the main carriage, together the main carriage and the cassette are able to be driven inwardly with respect to the main chassis along a linear path from an open position wherein the main carriage is spaced from the fixed seat to a closed position to engage the cassette to the fixed seat; and a position sensor being operatively associated with the main carriage for tracking the position of the main carriage from the open position to the closed position;

wherein the fixed seat establishes the vertical and lateral position of the cassette, and the fixed seat and main carriage dictate the inward position of the cassette by pressing the cassette and the fixed seat against a common surface of the main carriage.

2. The medical pump of claim 1, further including an actuator connected to the main carriage to automatically move the main carriage, and a processing unit connected to the position sensor to receive position data from the position sensor; the processing unit also being connected to the actuator to receive electrical load data from the actuator, wherein the processing unit detects jam conditions in the medical pump by processing the position data and the electrical load data.

3. The medical pump of claim 1, wherein the position sensor is a non-contact sensor.

4. The medical pump of claim 3, wherein the position sensor is a linear pixel array that is attached to the chassis and continuously tracks the position of the main carriage.

5. The medical pump of claim 4, wherein the main carriage includes a position plate and the position sensor tracks a portion of the position plate to track the position of the main carriage.

6. The medical pump of claim 5, wherein the position plate has a slot formed therein and the portion of the position of the position plate tracked by the position sensor is the slot.

7. The medical pump of claim 1, wherein the main carriage floats with respect to the main chassis allowing the fixed seat to dictate the position of both the main carriage and cassette when the main carriage is in the closed position.

* * * * *